United States Patent [19]
Wallace et al.

[11] Patent Number: 5,915,380
[45] Date of Patent: Jun. 29, 1999

[54] SYSTEM AND METHOD FOR CONTROLLING THE START UP OF A PATIENT VENTILATOR

[75] Inventors: Charles L. Wallace, Encinitas; Warren G. Sanborn, Escondido; David Arnett, Half Moon Bay, all of Calif.; Howard L. Ferguson, Elk, Wash.; Jay Butterbrodt, Lawrenceberg, Ind.

[73] Assignee: Nellcor Puritan Bennett Incorporated, Pleasanton, Calif.

[21] Appl. No.: 08/818,808

[22] Filed: Mar. 14, 1997

[51] Int. Cl.[6] .................................................. A61M 16/00
[52] U.S. Cl. ............................. 128/204.21; 128/204.23; 128/204.18; 128/203.12
[58] Field of Search ..................... 128/204.21, 204.23, 128/204.18, 203.12, 204.26, 205.12, 203.14; 600/529, 532

[56] References Cited

U.S. PATENT DOCUMENTS

| | | | |
|---|---|---|---|
| 4,211,221 | 7/1980 | Schwanbom et al. | 128/204.26 |
| 4,340,044 | 7/1982 | Levy et al. | 128/204.21 |
| 4,440,177 | 4/1984 | Anderson et al. | 128/205.12 |
| 4,444,201 | 4/1984 | Itoh | 128/204.23 |
| 4,917,080 | 4/1990 | Bayerlein | 128/204.23 |
| 5,107,831 | 4/1992 | Halpern et al. | 128/204.23 |
| 5,231,981 | 8/1993 | Schreiber et al. | 128/204.21 |
| 5,398,676 | 3/1995 | Press et al. | 128/204.21 |
| 5,452,714 | 9/1995 | Anderson et al. | 128/204.21 |
| 5,458,137 | 10/1995 | Axe et al. | 128/204.21 |
| 5,626,151 | 5/1997 | Linden | 128/897 |
| 5,685,318 | 11/1997 | Elghazzawi | 600/529 |

FOREIGN PATENT DOCUMENTS

| | | |
|---|---|---|
| 0 099 743 | 2/1984 | European Pat. Off. . |
| 0 661 071 | 7/1995 | European Pat. Off. . |
| 2 729 084 | 7/1996 | France . |
| 8801322 | 12/1989 | Netherlands . |
| 96/11717 | 4/1996 | WIPO . |
| 97/06844 | 2/1997 | WIPO . |

OTHER PUBLICATIONS

International Search Report RE PCT/US98/03755, Dated Mar. 7, 1998.
Dräger—Evita Intensive Care Ventilator Instruction Manual.
Marketing Brochure—Pediatric–Adult Star 1500 Ventilator—Infrasonics, Inc. Star Products.

*Primary Examiner*—John G. Weiss
*Assistant Examiner*—V. Srivastava
*Attorney, Agent, or Firm*—Fulwider Patton Lee & Utecht, LLP

[57] ABSTRACT

The invention is directed to a ventilation control system for controlling the ventilation of a patient. The ventilation control system utilizes a user-friendly user interface for the display of patient data and ventilator status, as well as for entering values for ventilation settings to be used to control the ventilator. Values for ventilation settings entered during set up of the ventilator result in the display of only those further ventilation settings that are appropriate in accordance with the earlier entered settings.

12 Claims, 9 Drawing Sheets

SYSTEM AND METHOD FOR CONTROLLING THE START UP OF A PATIENT VENTILATOR

BACKGROUND OF THE INVENTION

1. Field Of The Invention

This invention relates generally to the field of medical equipment for respiratory therapy and more specifically to the user interface for a ventilator used for monitoring and controlling the breathing of a patient.

2. Description Of The Related Art

Modern patient ventilators are designed to ventilate a patient's lungs with breathing gas, and to thereby assist a patient when the patient's ability to breathe on his own is somehow impaired. As research has continued in the field of respiration therapy, a wide range of ventilation strategies have been developed. For example, pressure assisted ventilation is a strategy often available in patient ventilators and includes the supply of pressure assistance when the patient has already begun an inspiratory effort. With such a strategy, it is desirable to immediately increase the pressure after a breath is initiated in order to reach a target airway pressure for the pressure assistance. This rise in pressure in the patient airway which supplies breathing gas to the patient's lungs allows the lungs to be filled with less work of breathing by the patent. Conventional pressure assisted ventilator systems typically implement a gas flow control strategy of stabilizing pressure support after a target pressure is reached to limit patient airway pressure. Such a strategy also can include programmed reductions in the patient airway pressure after set periods of the respiratory cycle in order to prepare for initiation of the next patient breath.

As patient ventilator systems and their various components, including sensors and control systems, have become more sophisticated, and more understanding is gained about the physiology of breathing and the infirmities and damage which form the requirements for respiratory therapy, the number of variables to be controlled and the timing and interrelationships between the parameters have begun to confront the caregiver with a daunting number of alternative therapeutic alternatives and ventilator settings. Also, in such a complex environment, the interface between the ventilator and the caregiver has often not been adaptable to the capabilities of the operator, thus running the chance of either limiting the choices available to a sophisticated user or allowing a relatively less sophisticated user to chose poorly from the alternatives presented. Thus, it would be beneficial if a ventilator interface guided the user through the setup or therapy modification process, illustrating the relationship between changes, preventing incorrect or dangerous settings and sounding alarms or other audible indications of invalid settings when something is about to done that exceeds limits, but also allowing the advanced and sophisticated user to gain access to the full range of ventilator capabilities through an interface which both presents the various parameters and allows the visualization of their relationships.

Clinical treatment of a ventilated patient often requires that the breathing characteristics of the patient be monitored to detect changes in the breathing patterns of the patient. Many modern ventilators allow the visualization of patient breathing patterns and ventilator function and the caregiver adjusts the settings of the ventilator to fine tune the respiratory strategy being performed to assist the patient's breathing. However, these systems have been, up until now, relatively difficult to use by the unsophisticated user unless a limited number of options are selected. For example, in one prior art system, only a single respiratory parameter may be altered at a time. Moreover, the various respiratory parameters must often be entered into the ventilator controller in a prescribed order, or, where no order is prescribed, certain orders of entry should be avoided, otherwise the intermediate state of the machine before entry of the remaining parameters may not be appropriate for the patient. This inflexible approach to ventilator setup requires additional time and training if the user is to quickly and efficiently use the ventilator in a critical care environment.

Previous systems have also been deficient in that it is often difficult to determine the underlying fault that has caused an alarms to be sounded, and what controls or settings should be adjusted to cure the problem causing the alarm. For example, prior alarm systems have consisted of nothing more than a blinking display or light with an alarm to alert the user that a problem existed. Similarly, many prior art systems provided only limited assistance to a user or technician in setting the parameters to be used during treatment. For example, if a technician attempted to enter a setting that was inappropriate for the patient because of body size or for some other reason, the only alarm provided may have been an auditory indication that the value was not permitted, but no useful information was provided to assist the technician in entering an appropriate setting.

One problem consistently presented by prior art ventilator control systems has been that the user interface has offered relatively little to guide and inform the user during the setup and use of the ventilator. Prior systems typically utilized a single visual display of the operating parameters of the ventilator and sensed patient parameters. Alternatively, prior systems may have numerous fixed numeric displays, certain of which may not be applicable during all ventilation therapies. Even when more than one display has been provided, users typically received limited feedback, if any, from the control system indicating the effect that changing one particular setting had on the overall respiratory strategy. If a parameter was to be adjusted, the display would change to display that particular parameter upon actuation of the appropriate controls, and allow entry of a value for that parameter. However, the user was provided with no visual cue as to how the change in the parameter value would effect the overall ventilation strategy, and thus had no assistance in determining whether the value entered for the parameter was appropriate for the patient.

What has been needed and heretofore unavailable in patient ventilators is a user friendly graphic interface that provides for simultaneous monitoring and adjustment of the various parameters comprising a respiratory strategy. Such an interface would also preferably guide sophisticated users in implementing ventilation therapies, provide guidance on the relationships between parameters as they are adjusted, allow rapid return to safe operation in the event that an undesirable strategy was inadvertently entered, provide alarms that are easily understood and corrected and present all of the relevant information in an easily understood and graphic interface. The present invention fulfills these and other needs.

SUMMARY OF THE INVENTION

Briefly, and in general terms, the present invention is directed to a graphic user interface system for controlling a computer controlled ventilator to provide respiratory therapy to a patient. In a broad aspect of the invention, the invention includes a digital processor, a touch sensitive display screen and entry means cooperating to provide a user-friendly graphic interface for use in setting up and carrying out a wide variety of respiratory therapies. The processor controls the displaying of a plurality of screens, including user selectable graphic on-screen buttons for setting the values of various ventilator operating parameters for controlling the ventilator. Depending on the on-screen button touched, the processor causes different graphics to be displayed on the screens, provides graphic representations of the effect on the overall respiratory strategy caused by changes to the settings, and may also provide displays of patient data, alarm conditions, and other information.

In one preferred embodiment of the invention, the system includes the use of a digitally encoded knob for altering selected and displayed values of ventilation parameters, with the acceptable values indicated and unacceptable values alarmed and/or limited to prevent harm to the patient. The digital encoded rotation of the knob may be analyzed by the processor and a magnification factor applied to the knob output to increase the speed with which displayed values are altered. The magnification factor may also be used in the event of an overshoot condition to assist a user in recovering from the overshoot.

In another preferred embodiment of the invention, the processor may detect the connection of a patient to the ventilator when the ventilator is powered-up. The processor may then, in response to such a detection, start up the ventilator using a predetermined set of ventilator control settings deemed to be safe for the widest possible variety of patients.

In a further preferred embodiment of the invention, the processor may only display ventilator control settings appropriate for a selected mode of ventilation. The ranges of values of the appropriate settings, or bounds of the ventilation, may be limited by the processor in response to the selected mode of ventilation such that only those values determined to be appropriate are displayed, thus limiting the opportunity to select incorrect settings. Additionally, the processor may be responsive to specific values entered for certain of the ventilator settings to adjust the ranges of values allowed for ventilator settings dependent on the certain settings. Further, the processor may be programmed to require that a so called "ideal body weight" be entered before beginning ventilation of a patient, and then only ranges of values for settings that would be appropriate for ventilation of a patient with that ideal body weight are displayed.

In another presently preferred embodiment of the invention, the graphic user interface system includes at least two touch sensitive screen displays, a plurality of manual parameter controls, including at least one control knob that is activated upon selection of a parameter to be controlled and displayed on the screen, and a microprocessor controller which controls the logic and arrangement of the screen displays and the interface with the ventilator. The system of the invention includes protocols programmed into the microprocessor for entry of parameters within ranges predetermined to be appropriate for the patient parameters entered, alarms and other audible indications of invalid entry associated with entries outside of the acceptable ranges of parameters or inappropriate operation such as startup with a patient connected to the ventilator, and the ability to lock selected parameters while allowing for user variation of other parameters.

In another presently preferred embodiment of the invention, the user is provided a graphic interface in which the user is allowed to view and adjust a variety of alarm limits and is able to vary the levels at which the alarms are set off, within limits that are preset by the programming of the microprocessor as representative of values that are not to be exceeded, either as a function of ideal body weight or general parameters for all patients. The resultant setting of a filtered set of alarms may then be used by the user to avoid the setting of parameters that are likely to result in patient distress or other problems with the therapy, while still allowing the sophisticated user to configure a therapy that is customized for the particular patient.

In one presently preferred embodiment, the invention also allows the user an "undo" option in which a previously successful setting is reestablished after the user realizes that a series of proposed changes are likely to unworkable for the patient.

In yet another presently preferred embodiment of the invention, the user is provided with alarm indicators indicating the severity of a particular alarm. Alarm messages are also displayed in a selected screen area of the graphic user interface to assist the user in alarm recognition and understanding. Each alarm message may comprise an identifying message identifying the alarm being indicated, an analysis message providing information about the condition that caused the alarm to be indicated, and a remedy message suggesting steps that may be taken by the user to correct the alarm condition.

In a further currently preferred embodiment of the invention, the processor allows the user to configure the graphic user interface to provide a display of the current and/or proposed breath parameters and a graphic representation of the breath timing controlled by those parameters. Such a display allows the visualization of relationships between breath parameters, and, while parameters are being changed, provides the user with a visual representation of the effect of the proposed changes on the ventilation strategy while simultaneously allowing the user to view current settings, thus allowing the user to simultaneously view "where they are now" and "where they are going to be."

From the above, it may be seen that the present invention represents a quantum leap forward in the user interface available for patient ventilation. While assisting the sophisticated user in both visualizing the ventilation strategy and performance of the patient on the ventilator, it also guides and controls the less sophisticated user in setup and understanding of the relationships between ventilator settings. The invention provides these benefits while enforcing fail-safe functioning in the event of a variety of inadvertent or erroneous settings or circumstances.

These and other features and advantages of the invention will become apparent from the following detailed description, taken in conjunction with the accompanying drawings, which illustrate, by way of example, the features of the invention.

BRIEF DESCRIPTION OF THE DRAWINGS

In the drawings, where like reference numerals indicate like or similar components, elements and features across the several figures.

DETAILED DESCRIPTION OF THE PREFERRED EMBODIMENTS

The present invention as disclosed in the exemplary drawings is embodied in a gaphic user interface for a patient ventilator which guides the user through the start up procedure for a new patient. More specifically, the invention is embodied in a graphic user interface which displays ventilation and patient respiration parameters and allows the entry of commands to initiate ventilator startup configuration. The invention includes a digital processor and memory which provides start up protocols and prompts to the screen which guide the user in setting up the ventilator for the patient. The displays are designed to arrange the screens and control buttons in a logical grouping which avoids confusion and limits the opportunity for mistakes. The invention also includes a startup protocol wherein the processor controls the ventilator using a set of ventilator parameters that have been determined to be appropriate for the widest variety of patients in the event the ventilator detects that a patient is already connected to the ventilator when the startup procedure is commenced to ensure that the patient is not ventilated using inappropriate ventilation parameters.

The exemplary drawings will now be described in more detail, wherein like referenced numerals refer to like or corresponding elements among the several drawings.

Figure 1:
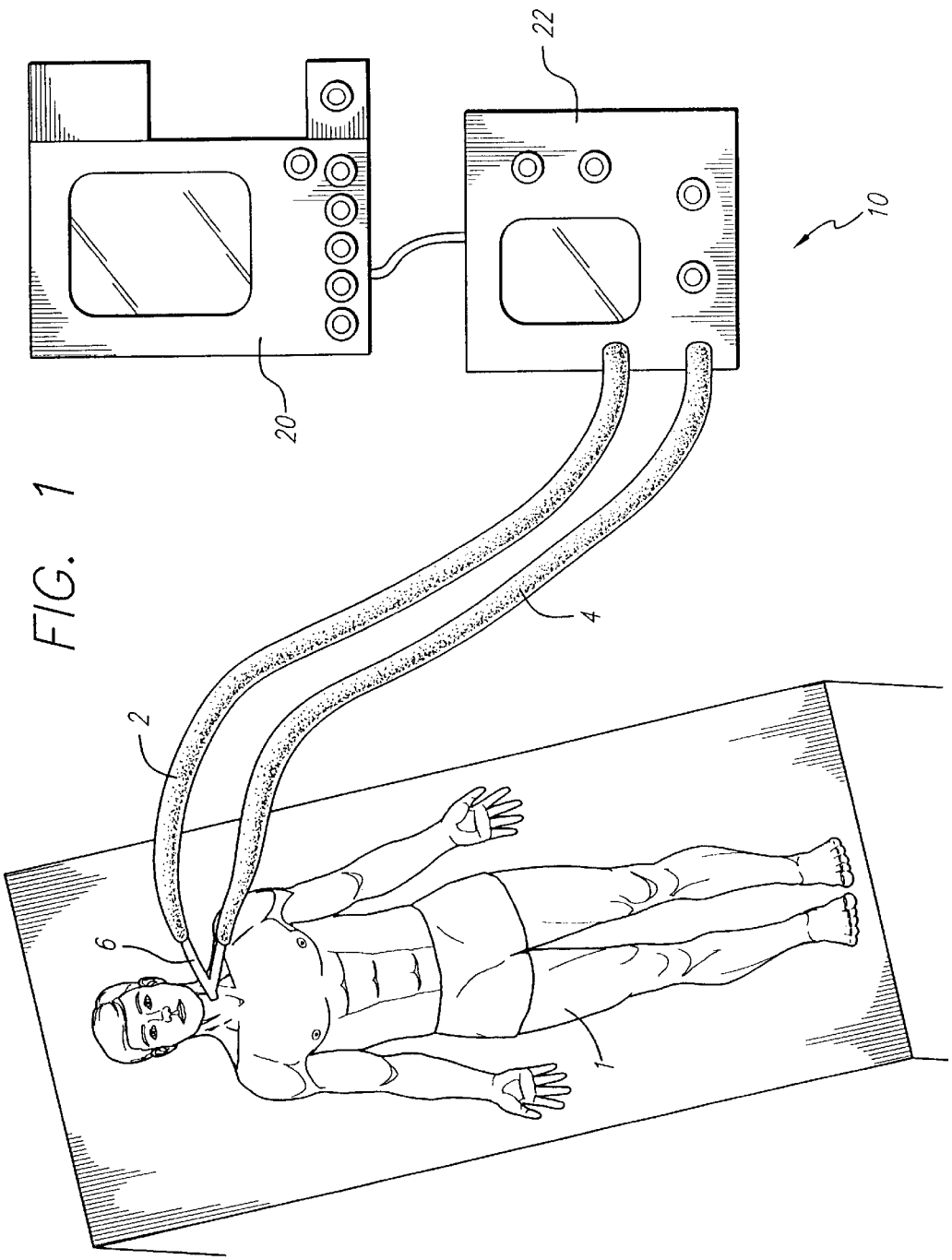
FIG. 1 is a schematic diagram of showing a patient receiving respiratory therapy from a ventilator system comprising a graphic user interface and a respirator constituting one embodiment of the present invention.

FIG. 1 shows a patient 1 receiving respiratory therapy from a ventilator system 10 having a graphic user interface 20 connected to and controlling a breath delivery unit, or respirator 22. The patient is connected to the respirator 22 by a patient circuit comprising an inspiratory line 2, and expiratory line 4, and a patient connection tube 6, all connected by a patient connector (not shown) of a type well-known in the art. The respirator 22 includes a processor or controller 60 which controls the real-time operation of the respirator 22.

Figure 2:
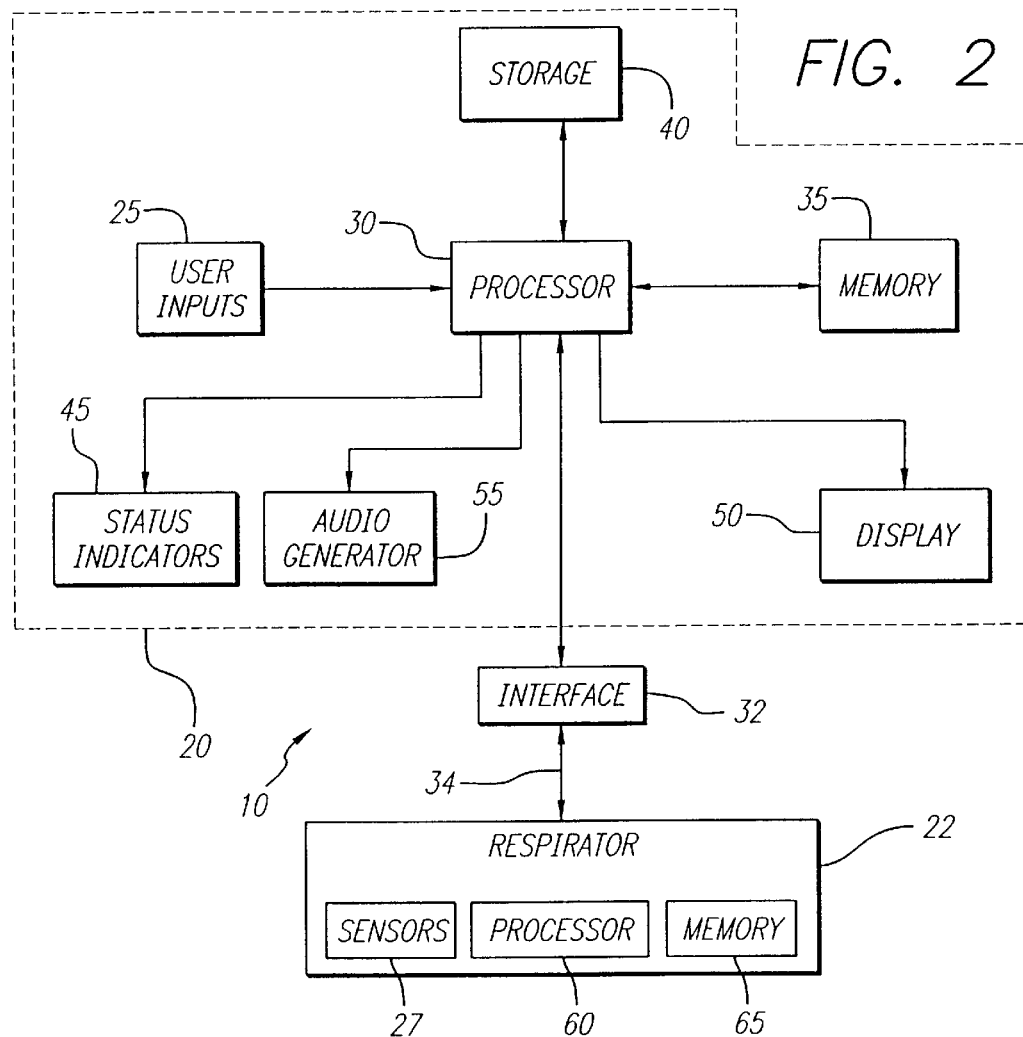
FIG. 2 is a schematic diagram, primarily in block form, of the various subsystems of of the graphic user interface shown in FIG. 1.

FIG. 2 depicts the graphic user interface 20 of FIG. 1 in more detail. Generally, the graphic user interface 20 comprises user inputs 25, a processor 30 and memory 35 comprising read only memory, random access memory or both. The memory 30 may be used to store current settings, system status, patient data and ventilatory control software to be executed by the computer. The processor 30 may also be connected to a storage device, such as battery protected memory, a hard drive, a floppy drive, a magnetic tape drive or other storage media for storing patient data and associated ventilator operating parameters. The processor 30 accepts input received from the user inputs 25 to control the respirator 22. The ventilation control system 20 may also include status indicators 45, a display for displaying patient data and ventilator settings and an audio generator for providing audible indications of the status of the ventilator system 10.

The memory 35 and a memory 65 associated with the respirator processor 60 may be non-volatile random access memory (NVRAM) for storing important, persistent variables and configuration settings, such as current breath mode setup. Typically, during normal operation of the ventilation control system 20, such an NVRAM functions similarly to a typical random access memory. If, however, a low-voltage condition is detected, such as may occur during a brown-out or at the beginning of a power failure, the NVRAM automatically stores its data into non-volatile storage.

The graphic user interface 20 includes an interface 32 for providing control signals from the processor 30 to the respirator processor 60 of the respirator 22, and also for receiving signals from sensors 27 associated with the respirator 22 indicative of patient condition and the status of the respirator 22. The processor 30 of the graphic user interface 20 may also receive input representative of various clinical parameters indicating clinical condition of the patient 1 and the status of the respiratory therapy from the sensors 27 in the respirator 22. The interface may include, for example, an ethernet connection of a RS-232 serial interface. A cable 34 having an appropriate number of conductors is used to connect the respirator 22 to an appropriate connector (not shown) of the interface 32.

Figure 3:
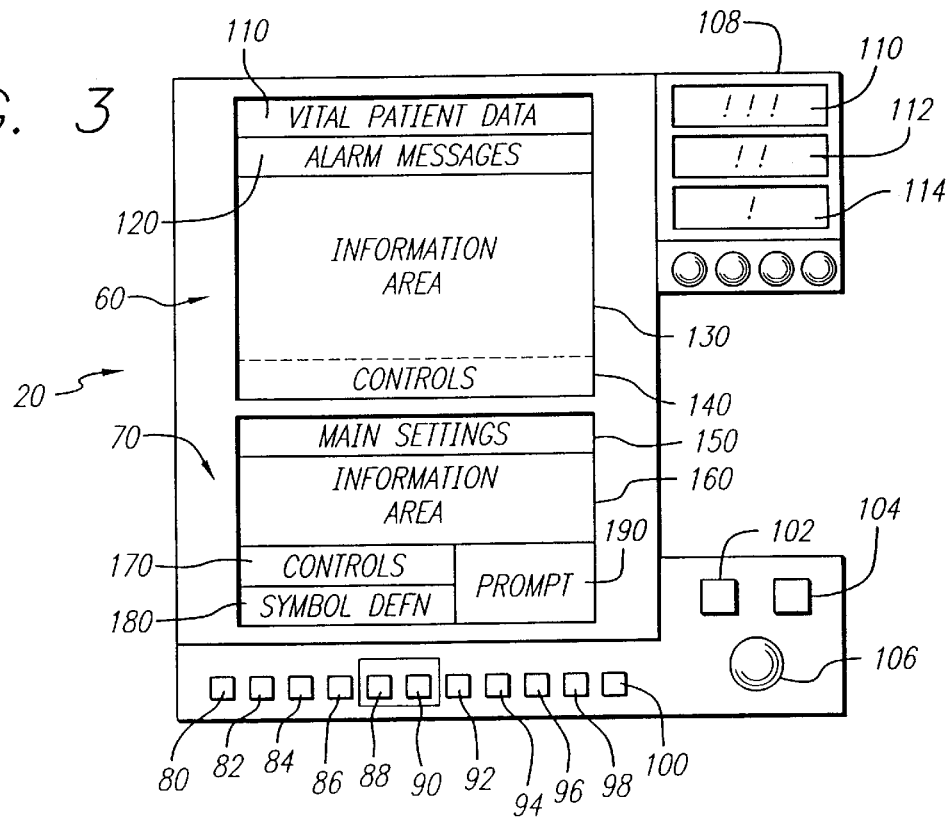
FIG. 3 is frontal plan view showing external details of graphic user interface of FIG. 1.

A preferred embodiment of the display 50 incorporating a user interface is illustrated in FIG. 3. Generally, the display 50 comprises an upper display 60 and a lower display 70, dedicated keys 80, 82, 84, 86, 88, 90, 92, 94, 96, 98, 100, 102, 104 and knob 106. As will be described in more detail below, additional user inputs are dynamically provided by on-screen buttons that are drawn on the upper and lower displays 60 and 70. Typically, each dedicated key or on-screen button includes, within the outline of the button, either a graphic icon or text identifying the purpose of the button to the user. These graphic icons or text enhance the ease of use of what would otherwise be a confusing array of user inputs. Moreover, the use of graphic icons or text to identify the function of dynamically generated on-screen buttons provides for virtually unlimited opportunities to add functions to the graphic user interface 20 by upgrading the programming of the processor 30 as new functions are desired by the users of the system. Additionally, the use of graphic icons overcomes the potential problem of identifying the functions of a button where language comprehension may be a problem, such as the use of the ventilator in a country where English is not readily understood.

Referring again to FIG. 3, key 80 is identified with a graphic design in the form of a stylized padlock. Actuation of key 80 by an operator locks the keys and buttons of the graphic user interface 20 to prevent inadvertent altering of the settings of the system. Keys 82 and 84 control the contrast and brightness of the displays 60, 70. Key 86 bears a stylized graphic design representative of a speaker emitting sound, and a graphic indicative of a volume control. Thus, key 86 is easily identifiable as a control for altering the loudness of audible alarm signals provided by the graphic user interface 20. Key 92 bears a "?" and actuation of key 92 activates a help system to assist a user in operating the graphic user interface 20.

Keys 94, 96, 98 and 100 control various aspects of the ventilator, and are used by an operator to override the automatic settings of the graphic user interface 20. When key 94 is pressed, the processor 30 of the graphic user interface 20 provides a signal over the 32 to the processor in the respirator 22 instructing the respirator processor to ventilate the patient with 100% oxygen for two minutes. The processor in the respirator 22 also starts a timer and causes the value of the time at any given instant to be written to a memory associated with the respirator processor. When the value in the respirator memory is equal to two (2) minutes, indicating that the 100% oxygen gas mixture has been provided to the patient for two (2) minutes, the respirator processor controls the respirator 22 to stop the flow of the 100% oxygen to the patient. If the user presses key 94 during the two (2) minute duration of the 100% oxygen ventilation, the value of the time stored in the memory is reset to "0" and timing continues for an additional two minutes. Typically, the respirator processor may be programmed to respond to any number of actuations of key 94 without prompting the user for validation or before sounding and displaying an alarm. Alternatively, the respirator processor may be programmed to respond to only a limited number of actuation of key 94 before sending a signal through the interface 32 to the processor 30 of the graphic user interface 20 requesting the processor 30 to provide a visual prompt on the display 50 and/or to control the audio generator 55 to sound an audible alarm indicating that an allowed number of actuations of key 94 has been exceeded.

When key 96 is pressed during an exhalation, the processor 30 controls the ventilator to immediately provide an inspiration. Actuation of key 98 results in an extension of the expiration phase. Similarly, actuation of key 100 results in a lengthening of the inspiration phase.

Key 102 is labeled with the text "Clear" and actuation of key 102 causes proposed changes to the value of a currently selected setting, to be discussed in more detail below, to be cleared. Key 104 is labeled with the text "Accept." When key 104 is touched, any proposed changes to the ventilator settings are confirmed, and become the current ventilator settings.

Knob 106 is used to adjust the value of an individual setting selected by pressing either keys 82, 84 and 86 or certain on-screen buttons. Knob 106 is mounted on a shaft whose rotation is digitally detected by a rotary encoder/decoder, such that the processor 30 receives signals indicating not only the magnitude of the rotation of knob 106, but also the speed and rate of acceleration and deceleration of the rotation of knob 106. These signals are interpreted by the processor 30 to display allowable values for the selected setting. In one embodiment of the present invention, the processor 30 is responsive to the signals indicative of the speed of rotation of knob 106 to calculate a velocity based magnification factor dependent on how fast and how long the user turned the knob that is applied by the processor 30 to adjust the increment of the values displayed. The processor 30 uses this magnifying factor to increment the displayed values in larger increments when knob 106 is rotated rapidly, and incrementing the displayed values in smaller increments when knob 106 is rotated slowly.

A common problem using rotating knobs where a magnification factor is applied in this manner is that there is inevitable "overshoot" of the desired value. Following an overshoot, the user must reverse the direction of rotation of the knob. This reduces the speed of rotation of the knob to zero, and eliminates the magnification. Elimination of the magnification, however, results in more rotation and time to recover from the overshoot. One novel aspect of the present invention is that the processor 30 does not reduce the magnification factor to zero when the knob is counter rotated, as described above. Rather, the processor 30 applies a magnification factor to the counter rotation to reduce the amount of rotation of the knob 106 necessary to recover from the overshoot. The processor sets a time-based limit on how quickly the magnification factor is allowed to decrease, thus ensuring that some magnification remains during overshoot recovery.

Additionally, the processor 30 may provide signals to the audio generator 55 to cause the audio generator 55 to provide an audible indication of the rotation of knob 106. For example, the audio generator 55 may generate a "click" for a predetermined amount of rotation of the knob 106 or to signify that an on-screen button or dedicated key has been actuated. The audio generator 55 may also provide an audio signal to the user if the maximum or minimum value of the range of values for the selected setting has been reached, indicating that further rotation of the knob 106 will not cause any larger or smaller values to be displayed.

Referring again to FIG. 3, the display area of the ventilation control system 20 comprises an upper display 60 and a lower display 70. The upper display 60 is divided into four non-overlapping areas. These areas are "vital patient data" area 110, an "alarm message" area 120, an "information area" 130 and a "controls" area 140. Area 130 is a multi-purpose area that may be used to display, for example only, screens depicting current alarms, an alarm history log, real-time waveforms, measured patient data that is not otherwise displayed in the vital patient data area 110, quick reference information, a log of diagnostic codes, operational time for system components, a ventilator test summary, the current ventilator software/hardware configuration, a log of the results from running a short self test, apnea ventilation settings and safety ventilation settings.

Similarly, the lower display 70 is divided into five non-overlapping areas. These areas are a "main settings" area 150, an "information area" 160, a "controls" area 170, a "symbol definition" area 180 and a "prompt" area 190. Examples of information displayed in area 160 include, but are not limited to screens displayed during ventilator startup and ventilator setup, apnea setup, alarm setup, new patient setup, communications setup, date/time setup, miscellaneous setting not otherwise shown in the main settings area 150 and breath timing graphs.

It will be understood that the labeling of the four non-overlapping areas of the upper display 60 and the labeling of the five non-overlapping areas of the lower display 70 are not critical to the present invention, but are for convenience only. Thus, the areas could have other labels, depending on the information desired to be conveyed.

The display area also includes an alarm display area generally indicated by reference numeral 108. The alarm display area 108 includes a high urgency alarm indicator 110, a medium alarm urgency indicator 112 and a low urgency alarm indicator 114. The alarm urgency indicators 110, 112 and 114 may be light emitting diodes or any other means of providing a visual indication of an alarm. Additional indicators (not shown) may also be included below the alarm indicators.

Low urgency alarms are used to inform the user that there has been some change in the status of the patient-ventilator system. During a low urgency alarm, the low urgency alarm indicator 114 lights, an audible alarm having a tone indicating that a low urgency alarm event has occurred, and an alarm message is displayed in the alarm message area 120 of the upper screen 60. During a medium urgency alarm, the medium urgency alarm indicator lights, a medium urgency audible alarm is sounded, and an alarm message is displayed in the alarm message area 120 of the upper screen 60. Because medium urgency alarms typically require prompt attention to correct the cause of the alarm, the medium urgency indicator may flash, and the audible alarm may sound repeatedly with a distinctive tone.

High urgency alarms require immediate attention to ensure patient safety. During a high urgency alarm, the high urgency indicator 110, which may be colored red, flashes, a distinctive audible alarm is sounded and an alarm message is displayed in the alarm message area 120 of the upper screen 60.

Figure 4:
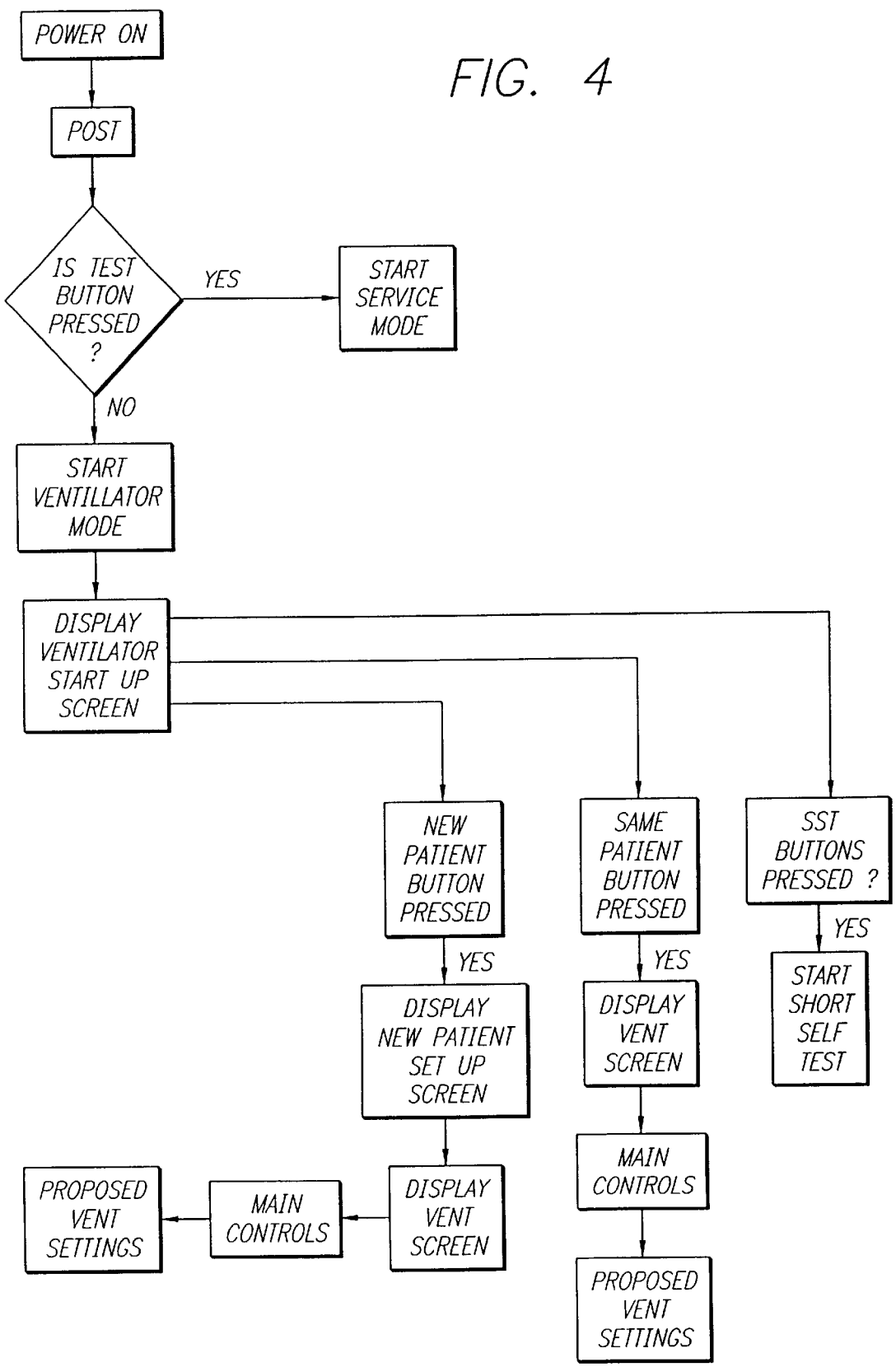
FIG. 4 is a schematic diagram, primarily in block form, of the sequence of display screens typically displayed by the graphic user interface of FIG. 3.

Referring now to FIG. 4, the overall hierarchical structure of the user interface comprising the keys, on-screen buttons and upper and lower display screens will be described. When the user of the ventilator turns on the power to the graphic user interface 20 and respirator 22 by actuating a power switch typically located on the respirator 22 (not shown), the processor 30 begins to power itself up by initiating a power on self test (POST). If the user actuates a test button, also typically mounted on the respirator 22 (not shown) during the time when the POST is running, the ventilator will start up in a SERVICE mode. If the test button is not actuated, the ventilator will start up in a VENTILATOR mode.

Figure 5:
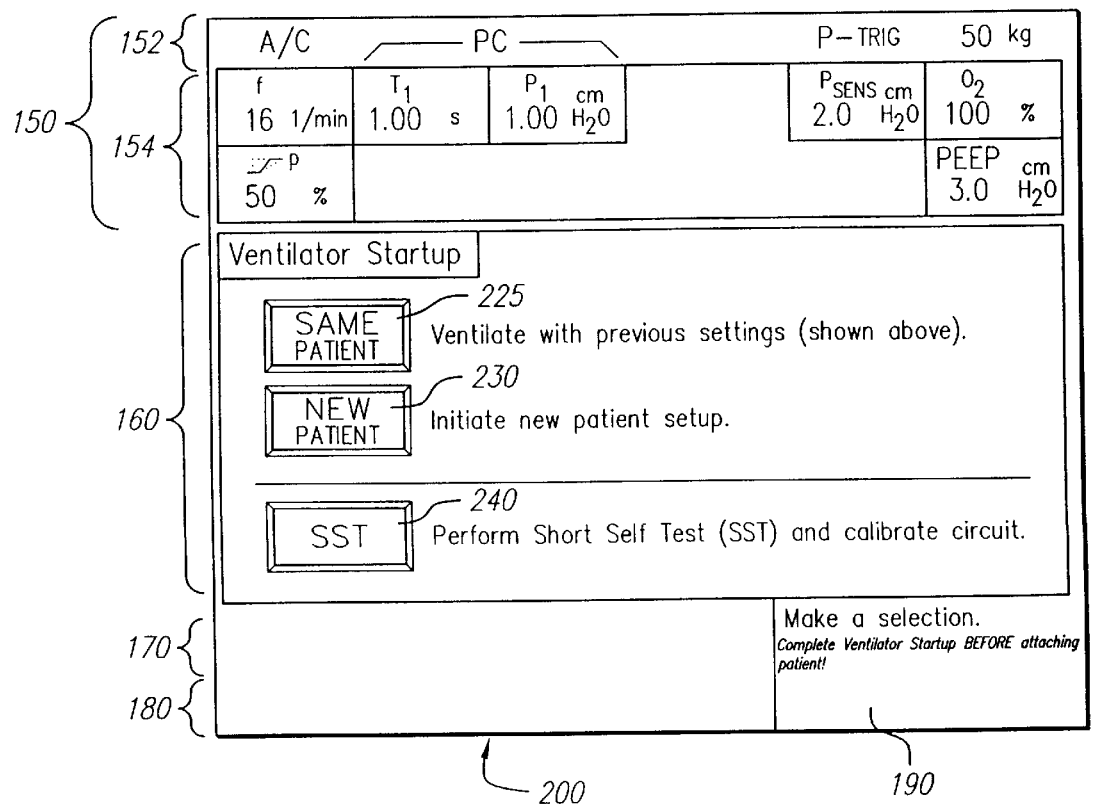
FIG. 5 is an illustration of a ventilator startup screen displayed upon startup of the graphic user interface of FIG. 3.

When the graphic user interface starts up in the VENTILATOR mode, the lower display 70 of the graphic user interface 20 displays the ventilator startup screen 200 depicted in FIG. 5. When the ventilator startup screen 200 is displayed, the main settings area 150 of the lower display has two subareas; the upper subarea 152 displays the main ventilator mode settings, while the lower subarea 154 displays the values of the ventilator settings appropriate to the main ventilator mode settings that were in use prior to powering down the graphic user interface 20 and respirator 22.

The control area 170 on the lower screen 70 typically contains one or more on-screen buttons (see FIG. 8), but is blank on the ventilator startup screen 200, as illustrated in FIG. 5. This illustrates the dynamic nature of the various screens that are presented to the user to assist the user in selecting ventilator settings appropriate to a given respiratory strategy. At this stage of the startup process, no settings other than those illustrated are presented to the user so that the user may not inadvertently enter an inappropriate ventilator setting. Other novel features of the display of the present invention further assisting the user will be described below.

A message instructing the user as to what action to take next is displayed in the prompt area 190. As indicated by the message displayed in the prompt area, it is important that the ventilator be setup before attaching the ventilator to a patient.

As is illustrated by display depicted in FIG. 5, on-screen buttons such as buttons 225, 230 and 240 that are active and may be touched by the user to initiate activity are displayed so that the on-screen buttons appear to have a raised, three dimensional appearance. In contrast, on-screen buttons whose actuation is not appropriate on a particular screen are displayed having a flat, non-three dimensional appearance, as, for example, the on-screen buttons displayed in subarea 154 of the main settings area 150.

The information area 160 of the ventilator startup screen 200 provides the user with three on-screen buttons to choose from to initiate the next step in completing the setup of the graphic user interface 20. The user may touch the SAME PATIENT on-screen button 225 followed by the off-screen ACCEPT key 104 to set up the ventilator with the settings displayed in the main settings area 150. If no previous patient settings are stored in the memory 35, the SAME PATIENT on-screen button will not be displayed. Alternatively, if the ventilator is being used to provide respiratory therapy to a patient different from the previously treated patient, the user may actuate the NEW PATIENT on-screen button 230. Actuation of the NEW PATIENT on-screen button 230 will result in the display of a new patient setup screen. The user may also choose to perform a short self test (SST) of the ventilator and the graphic user interface 20 by touching the SST on-screen button 240. The SST on-screen button 240 will not be displayed if the ventilator is already connected to a patient.

The upper display 60 and the lower display 70 incorporate touch sensitive screen elements, such as, for example only and not by way of limitation, infrared touch screen elements, to allow for actuation of on-screen buttons, such as on-screen buttons 205, 210, 215, 220, 225, 230 and 240. The touch screen elements and the processor 30 operate in coordination to provide visual cues to the user as to the status of the on-screen buttons. For example, as described previously, the on-screen buttons are displayed in such a manner as to appear to be three-dimensional. When one of the on-screen buttons is actuated by the user touching the display screen with a finger, a pencil or other instrument, the touch screen elements detect the application of the finger, pencil or other instrument and provide the processor 30 with signals from which the screen location where the touch occurred may be determined. The processor 30 compares the determined location of the touch with the locations of the various buttons displayed on the current screen stored in the memory 35 to determine the button, and thus the action to be taken, associated with the location of the touch. The processor then changes the display of the touched on-screen button to make the button appear to be depressed. The processor may also alter the display of the text incorporated into the three-dimensional on-screen button. For example, the SAME PATIENT text displayed on the on-screen button 225 normally appears as white letters on a dark or gray button when the button is in an untouched stated. When the button 225 is touched, the processor 30 may cause SAME PATIENT to be displayed as black letters on a white button. Additionally, the prompt area 190 may change to a white background with black letters to draw the user's attention to the prompt area 190 when a message is displayed in the prompt area 190.

Typically, the action initiated by touching an on-screen button is obtained when the user lifts the finger, pencil or other instrument from the surface of the display screen. However, the processor may also be responsive to a user sliding the finger, pencil or other instrument off the on-screen button and onto the remaining surface of the display screen to reset the on-screen button in its un-actuated state and to take no further action. Thus, the action initiated by the touching of the on-screen button may only be obtained when the finger, pencil or other instrument is lifted from the portion of the display screen that is displaying the on-screen button. This feature allows the user to abandon a button touch without activating the function associated with the button in the case where the button was touched inadvertently or in error.

When the NEW PATIENT on-screen button 230 is touched, the processor 30 responds by displaying a new patient setup screen (not shown) and purges any previously entered settings from the memory 35. The new patient setup screen includes an IBW on-screen button for displaying and altering the value for the ideal body weight (IBW) of the patient. The new patient setup screen also includes a CONTINUE on-screen button; however, the CONTINUE button is not displayed until the IBW button is touched to ensure that the user adjusts the IBW to a suitable value. The CONTINUE button is displayed immediately after the IBW button is touched. Thus, if the value for IBW currently stored in the memory 35 is acceptable, the IBW does not need to be adjusted, and the CONTINUE button may be touched to accept the current value of the IBW.

When the IBW on-screen button is touched, the value for IBW currently stored in the memory 35 of the graphic user interface 20 may be adjusted by the user by rotating the knob 106 to either increase or decrease the displayed value until the value for the IBW desired by the user is displayed. The user may then touch the CONTINUE button to store the new value for IBW in the memory 35. When the CONTINUE button is touched, the processor 30 responds by causing a vent setup screen to be displayed. Because the vent setup screen is being displayed in response to the completion of the new patient setup screen, the vent setup screen is displayed in a new patient mode, and is labeled accordingly.

The processor 30 is responsive to the entered value for the patients' IBW to determine the initial values and ranges, or bounds, of the values of the various ventilator settings that are appropriate for use with a patient having that IBW. For example, the range of appropriate values for the various ventilator settings differ between adults and children. The processor will display only values that fall within the appropriate range of values for selection by the user during setup dependent upon the IBW, and will not accept values for settings that fall outside of the determined range. If the user attempts to enter a value outside of the appropriate range for that patient's IBW, the processor 30 may provide an audible indication of an attempt to enter an out of range value and/or a prompt to the user that the value is inappropriate.

Figure 6:
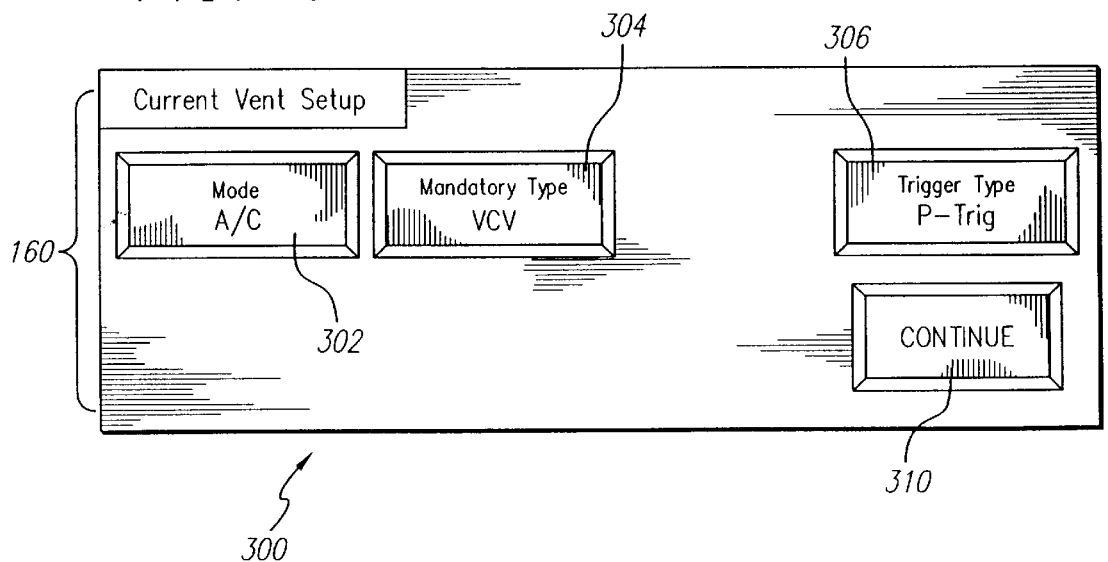
FIG. 6 is an illustration of a main controls setup screen used to set the main control settings of the ventilator of FIG. 3.
Figure 7:
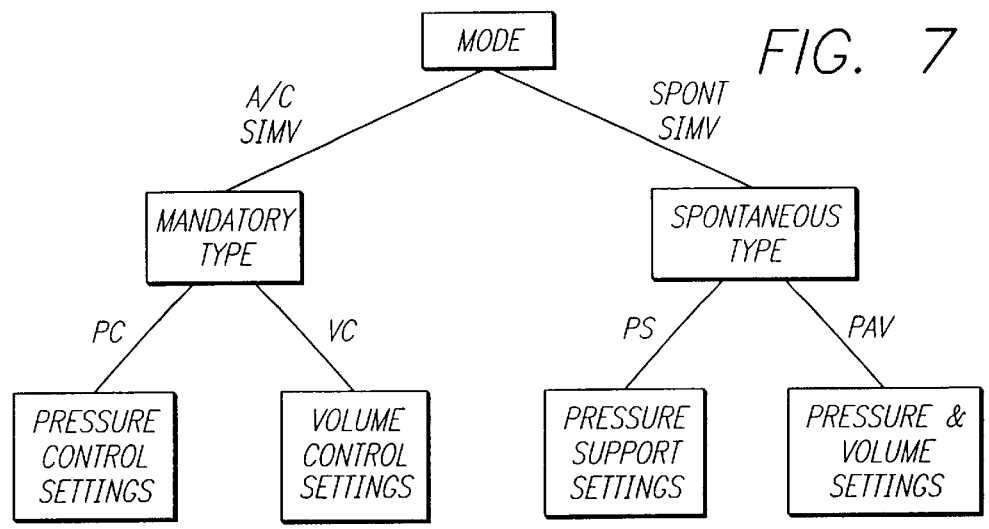
FIG. 7 is a schematic diagram, primarily in block form, illustrating how the adjustment of certain settings affects the applicability of other settings used to control the ventilator of FIG. 3.
Figure 8:
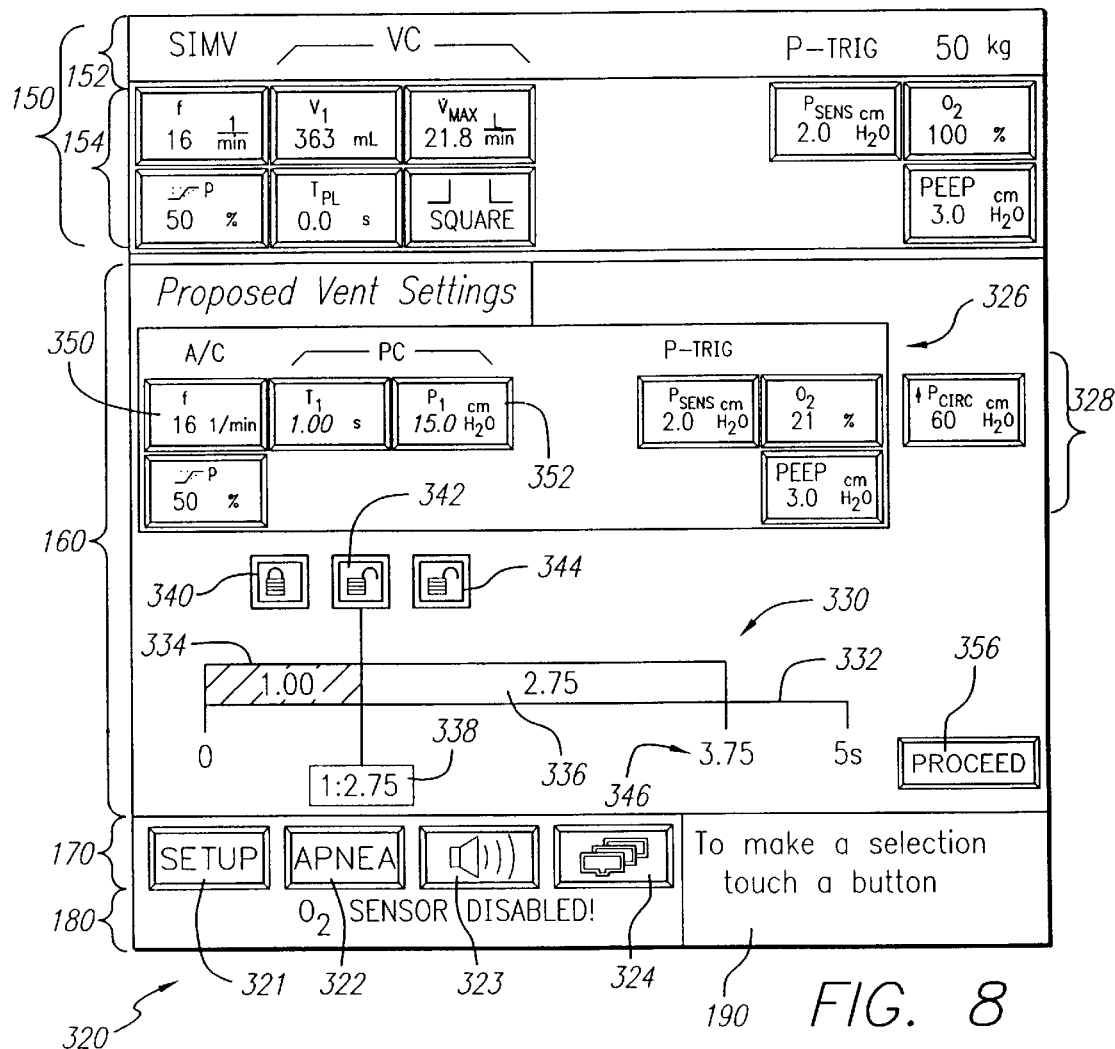
FIG. 8 is an illustration of a proposed vent settings screen including a breath diagram.

Referring now to FIGS. 6–8, the layout and functions of the vent setup screen will now be described. Traditionally, setting up a ventilator required a user to navigate through a number of confusing and complicated displays. A novel aspect of the present invention is the simplification of ventilator setup by hierarchically categorizing the ventilator controls and settings to minimize the number of choices available to a user on any one screen. The vent setup sequence used to configure the ventilator comprises two display phases. These two phases have been designed to simplify setup of the ventilator by grouping ventilator settings in logically arranged groups. Further, the settings entered during the first phase determine the settings presented to the user during the second phase. In this manner, only those ventilator parameters that are appropriate for the mode settings entered during the first phase are displayed. Additionally, the ranges of values, or bounds, of the displayed settings may be further limited as appropriate depending on the proposed ventilator mode and settings. Moreover, since some ventilator parameters may be dependent on the values selected for certain other ventilator parameters, the ranges of values for the dependent ventilator parameters may be limited in accordance with the settings of those independent ventilator parameters. In this manner, the user is presented only with those settings that are appropriate depending on settings already entered by the user. Such a hierarchical sequencing and presentation are useful in preventing the inadvertent entry of inappropriate ventilator settings.

Once a value for IBW has been entered, the subsequent phases of the New Patient Setup process are similar to the "Vent Setup" sequence of screens which may be accessed at any time during normal ventilation by touching button 321 (FIG. 8). For example, in the first phase of New Patient Setup, a screen is displayed entitled "New Patient Setup" instead of "Current Vent Setup" and is preceded by a screen presenting the proposed setting for IBW. Similarly, in the second phase, the title of the screen is "New Patient Settings" instead of "Current Vent Settings." Accordingly, the following discussion address the "Vent Setup" sequence.

When the vent setup screen is first activated, or following the IBW screen utilized during the new patient setup procedure described above, the Main Controls phase depicted in FIG. 6 is displayed. In the Main Controls phase, only buttons 302, 304 and 306, representing the main control settings, are visible in the information area 160 of the lower display screen 70. As shown in FIG. 8, however, the values for the currently selected main controls continue to be displayed in area 152, and the currently selected settings are displayed in area 154 of the main settings area 150 of the lower screen 70. The values displayed in areas 152 and 154 remain visible at all times during ventilation setup; thus it may be assumed that they are displayed unless specific reference is made to the display of different information in areas 152 and 154. When the main controls screen is being displayed during the "New Patient Setup" sequence, the on-screen buttons in area 154 of the main settings area 150 are displayed with a flat, non-three dimensional appearance, indicating that they cannot be actuated. During normal ventilation however, the on-screen buttons in area 154 may always be actuated by the user; thus they are displayed with a raised, three-dimensional appearance during normal ventilation.

As depicted in FIG. 7, the present invention decomposes the traditional mode setting into a simple mode plus separate "mandatory type" and "spontaneous type" settings. There are three modes: "A/C", or assist/control mode; "SIMV" or synchronous intermittent mandatory ventilation; and "SPONT", for spontaneous respiration. Dependent on the mode and type selected, the processor 30 will display only those settings appropriate to that mode and mandatory type. For example, if the user selects "A/C" mode and "PC" mandatory type, the processor 30 will display on-screen buttons for changing ventilator settings related to pressure control of the ventilation. Similarly, selecting "SPONT"

mode and "PS" spontaneous type results in the display of on-screen buttons for changing ventilator settings related to pressure support.

Referring again to FIG. 6, Button 302 is labeled with "Mode"; Button 306 is labeled with "Mandatory Type"; and Button 306 is labeled with "Trigger Type." Each of the buttons 302, 304 and 306 also display the setting currently selected for each of the main control settings. For example, button 302 displays "A/C" indicating that assist/control mode is selected. Alternatively, where SIMV or SPONT modes are currently selected, button 302 will display either SIMV or SPONT as appropriate. When either SIMV or SPONT modes are currently selected, a fourth button, button 308 (not shown) labeled with "Spontaneous Type" may also be displayed. Further, when the mode is set to SPONT, a message may be displayed below button 304 indicating that the value displayed on button 304, "Mandatory Type," applies to manual inspiration only.

As with others of the buttons used to make changes to the values of various operational parameters used by the processor 30 to control the respiratory therapy of a patient, the main control settings on the current vent setup screen are set by touching the desired one of the displayed buttons 302, 304, 306 or 308 (not shown), and then rotating knob 106 until the desired value is displayed. When the desired value for the setting is displayed, the user may provisionally accept and store that value in the memory 35 by touching the continue button 310. Alternatively, if more than one main control setting needs to be changed by the user, the user may defer touching the continue button 310, and may instead select among the other buttons to change the values of a different main control settings. The user may, if so desired, change the values of each of the main control settings. When the user has changed all of the desired main control settings, the changed values for each of the main control settings may be provisionally accepted, pending completion of the second phase of the ventilator setup procedure, and stored in the memory 35 simultaneously by touching the continue button 310. Thus, the values for the main control settings may be accepted and stored in a batch, rather than one setting at a time. This is advantageous in that entry of multiple settings is easier and less time consuming. Batch entry is also useful in that all of the proposed values for the main control settings are displayed, and may be checked for entry errors by the user before being committed storage in the memory 35.

When the continue button 310 is touched, the first phase of ventilator setup is complete and the second phase begins. In the second phase of ventilator setup, the processor 30 displays a proposed vent settings screen 320 to prompt the user to complete the vent settings phase of the setup procedure, as depicted in FIG. 8. The proposed vent settings screen is displayed in the information area 160 of the lower display 70 (FIG. 3). This screen includes a display 326 of the main control settings set in the first phase described above, and an area 328 where a plurality of buttons are displayed. The buttons displayed in the area 328 are for setting the values for particular ventilation parameters that are appropriate to the main control setting. Thus, the buttons displayed in area 328 are dependent upon the values selected for the main control settings in the first phase of the ventilator setup. This display of only those buttons whose settings are appropriate to their associated main control settings simplifies the display, thus aiding the user in setting up the ventilator and preventing inadvertent errors due to user confusion.

As with the main settings screen displayed during the first phase of the vent setup procedure, the user may select a parameter to change by touching one of the on-screen buttons, such as the "$P_I$" on-screen button 352. When the user touches button 352, the button appears to be depressed, and may change color and text contrast as described above. The user then adjusts the value of the setting by turning knob 106 (FIG. 3) until the desired value is displayed on the button 352. If the user is satisfied with the value entered for button 352, and the other displayed values, the user may touch the PROCEED button 356, followed by the ACCEPT key 104 (FIG. 3) to complete the vent setup procedure. Alternatively, the user may touch another one of the on-screen buttons, such as the "f" on-screen button 350. When button 350 is touched, button 352 "pops" up, indicating that button 352 is no longer selected, and button 350 appears to become depressed. An audible indication that the button is touched, such as a "click" may also be provided. In this manner, the values for all of the settings displayed may be changed one after another if desired, or only certain of the settings may be changed, as desired by the user. The user then may configure the ventilator to operate in accordance with all of the changed settings at once in a batch fashion by touching the PROCEED on-screen button 356, followed by pressing the off-screen ACCEPT key 104.

FIG. 8 further illustrates additional aspects of the graphical features provided by the user interface 20 that assist the user in setting up and operating the ventilator. As depicted in FIG. 8, the main settings area 152 displays the currently active main settings. These settings are easily compared with the main settings entered during the first phase of setup that are now displayed on the proposed vent settings screen in area 160. For example, as illustrated in FIG. 8, the ventilator is currently setup to ventilate in the SIMV mode, and the user has provisionally changed the mode to A/C, as indicated in the display 326. Another aspect of the invention is the visual prompt provided to a user that a particular setting has been changed. This aspect is illustrated by the change in the font used to display the value of the setting for "$P_I$", where the value "15.0" is displayed in italics, indicating that this value has been changed, compared to the normal font used to display the value "16" for "f", indicating that this value has not been changed.

If any of the main settings were changed during the first phase of the vent setup procedure were changed, the PROCEED on-screen button 356 is displayed on the proposed vent settings screen 320. Similarly, if none of the main settings were changed, the PROCEED on-screen button is not displayed until one of the settings displayed during the second phase of the vent setup procedure is changed. If the user is satisfied with the values for the settings that have been entered, the user may touch the PROCEED on-screen button 356. The user may then complete configuration of the ventilator settings, replacing the current vent settings with the proposed settings, by pressing the off-screen ACCEPT key 104. The off-screen placement of the ACCEPT key 104 ensures that no inadvertent changes are made to the ventilator settings.

If the processor 30 determines that the vent setup screen has been activated within a predetermined short period of time, for example, within 45 minutes of the most recent time the vent setup screen was used to change values of the ventilator settings, the processor 30 may display a PREVIOUS SETUP button on the main settings screen 300 (FIG. 6). The processor 30 removes this button from the screen if any changes are made using the screen. If the user touches the PREVIOUS SETUP button (not shown) on the main settings screen, a screen similar to the second phase display depicted in area 160 (FIG. 8) is displayed, showing values for the settings as they were immediately prior to the last setting change made using the vent setup screen. The on-screen settings buttons are all displayed in the flat, non-three dimensional state, indicating that they cannot be adjusted. A prompt message is displayed in area 190 explaining that accepting the displayed values will result in the entire previous setup being restored, including old alarm and apnea settings. The previous setup may be re-instated by the user by touching the PROCEED button 356, followed by pressing the ACCEPT key 104. This feature of the present invention allows a user to quickly restore the ventilator to the settings state it was in prior to a major setup change in the event that the altered ventilation strategy is not successful. A time lime is placed on the availability of the previous settings to avoid the possibility of re-imposing the settings when the patient's condition may have changed substantially. Individual changes to settings may be made to settings in the period following a major settings change without invalidating the settings stored for the previous setup. However, batch changes, that is, the changing of more than a single setting at a time, results in the stored previous settings being replaced with the most recent set of settings. This provides the user with the ability to fine tune the settings made during the major change without losing the ability to "UNDO" all of the major changes and return to the previous settings.

Referring again to FIG. 8, the proposed vent settings screen 320 also includes a graphical representation, or breath diagram 330, of the breath cycle that will be provided to the patient based on the settings entered by touching the buttons displayed in area 328 and adjusting the resulting displayed values using the knob 106, as described above. The breath diagram 330 includes a time line 332 that is displayed for scale purposes only, an inspiration bar 334 indicating the portion of the total breath duration during which inspiration will take place, an expiration bar 336 indicating the portion of the total breath duration during which expiration will take place, an inspiration/expiration ratio display 338 and a total breath time display 346. Besides the graphical representation of the duration of the inspiration and expiration portions of the total breath cycle, text representing the selected value for the durations may be displayed in the respective bars 334 and 336. For example, the inspiration phase of the breath is set to require 1.0 seconds and the expiration phase is set to require 2.75 seconds. The colors or shading of the inspiration bar 334 and the expiration bar 336 are preferably different to facilitate a user distinguishing between them. For example, the inspiration bar 334 may be shaded dark with white text, indicating that the breath timing parameter is "locked", while the expiration bar 336 may have grey shading and black text. It will be understood that this color scheme is only one example of a variety of color schemes that may be used to enhance the graphical representation of the breath cycle to provide a readily comprehensible display of either the current status of the ventilation or to assist a user in evaluating the effects of proposed changes to the ventilator settings.

Lock on-screen buttons 340, 342 and 344 are displayed above the time line 332 and display the lock status of the settings for the inspiration bar 334, the inspiration/expiration ratio 338 and the expiration bar 336 respectively. The user may change the lock status of the settings by selecting and touching one of the lock icons 340, 342, 344. For example, lock button 340 displays a graphical representation of a closed, or locked, padlock, while lock buttons 342 and 344 display graphical representations of open, or unlocked, padlocks. Touching lock button 340 will result in the lock button changing to the open, or unlocked state. Similarly, touching lock buttons 342 or 344 will result in the touched lock button changing to the closed, or locked, state. The effect of the "locked" setting is that the setting will not be automatically changed in accordance with a subsequent change in the breath rate parameter, while both of the settings for the "unlocked" parameters, here, the expiration time and the ration of inspiration to expiration, will be changed.

The display of the lock buttons is dependent upon the selected main control settings. For example, in the representative example depicted in FIG. 8, main control setting Mandatory Type is set to "PC", thus causing the lock buttons to appear; if the Mandatory Type is set to "VC", the lock bottons would not be displayed. When the Mandatory Type is "PC", only of the of the three "breath timing" settings, $T_I$, $T_E$ or I:E is displayed. $T_I$ is set by touching the on-screen button labeled $T_I$, and adjusting the knob 106 until a desired value is displayed. The value will be displayed both on the on-screen button $T_I$, and in the inspiration bar 334 of the breath diagram 330. Because the value for $T_I$ is locked, as evidenced by the closed lock button 340, and the dark shading of the inspiration bar 334, changes to the breath rate do not result in a change to the inspiration time; only the expiration time, inspiration/expiration ratio and the total breath time change. If another time parameter, such as $T_E$ was locked, changes to the rate would not affect $T_E$, but $T_I$ and the inspiration/expiration time ratio would change.

Figure 9A:
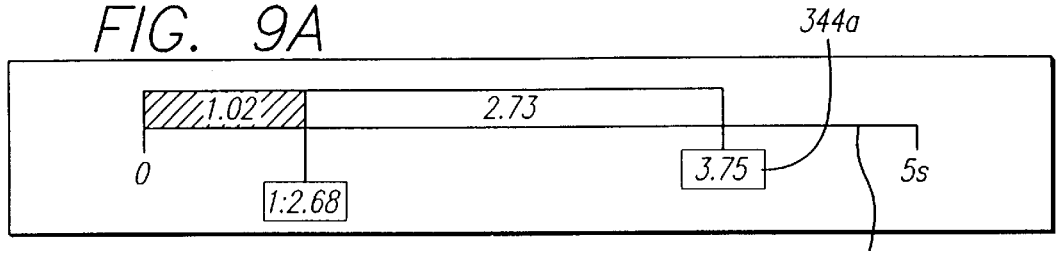
FIGS. 9A, 9B, and 9C are illustrations depicting the display of the breath diagram of FIG. 8 dependent upon the values of the parameters represented by the breath diagram.
Figure 9B:
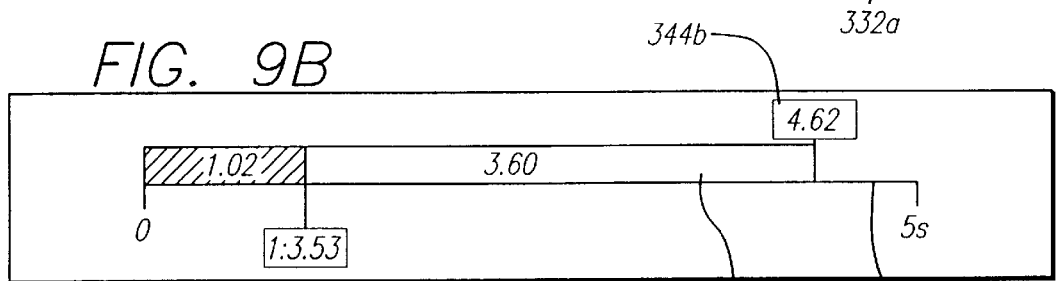
Figure 9C:
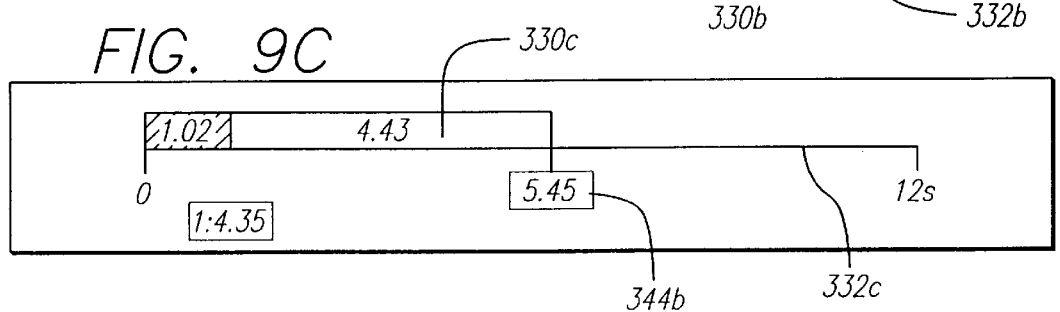

The above described relationship is apparent from FIGS. 9A–C. In FIG. 9B, the breath rate has been reduced; thus, the total breath time is increased, as indicated by the value in total time display 344b. Since the value for the inspiration time was locked, the relative length of the inspiration bar 334b did not change, while the relative length of the expiration bar 336b increased. A novel aspect of the present invention evident from the display depicted in FIG. 9B is the change in the location of the total breath time display 344b. In FIG. 9A, the total breath time display 344a is located below the time line 332a. In FIG. 9B, the expiration bar 336b has grown larger because of the increased breath time to the extent that the total breath time display 344b has approached the end of the time line 332b. The processor 30 maintains the location of each of the graphical features of the displays in the memory 35, and constantly assesses whether the display of a graphical feature, such as the breath diagram 330, on-screen buttons or text may possibly collide or overlap. In the case depicted in FIG. 9B, the processor 30 determined that the total breath time display 344b would be displayed sufficiently close to the end of the time line 332b that the total breath time display 344b would interfere with the display of the numerical scale of the time line 332b. Accordingly, the processor caused the total breath time display 344b to be displayed above the time line 332b to avoid such interference. It will be understood that the use of the total breath time display 344b is for purposes of example only. Any of the text or numeric values displayed in conjunction with the breath timing diagram 330 may be displayed as necessary to prevent interference with other graphical elements.

The processor 30 is also responsive to the values of the setting to change the scale of the time line 332 when appropriate. As depicted in FIG. 9C, the total breath duration 344c has been increased again, and is now greater than the previous scale of the time line 332c. Accordingly, the processor 30 has caused the time line 332c to be displayed with a larger scale. As the scale of the time line 332c enlarges, the relative lengths of the inspiration and expiration bars 334, 336 also change. As was described above, if the relative length of the inspiration bar 334c becomes too small to allow the display of the value of the inspiration time setting within the bar as depicted, the processor may cause the value to be displayed either above, below or to the left of the time line 332c in the vicinity of the inspiration bar 334c.

One advantage of a preferred embodiment of the invention is that the main control settings are displayed on both the vent setup screen and in the main setting area of the 152 of the lower display 150. Thus a user may adjust the main settings using either screen. However, it is particularly advantageous to make adjustments to the main control settings using the vent setup screen because only one main setting at a time may be changed in the main settings area 152, while multiple changes may be made in the vent setup screen and then accepted by the user and stored in the memory 35 of the graphic user interface 20 by the user as a batch.

Figure 10:
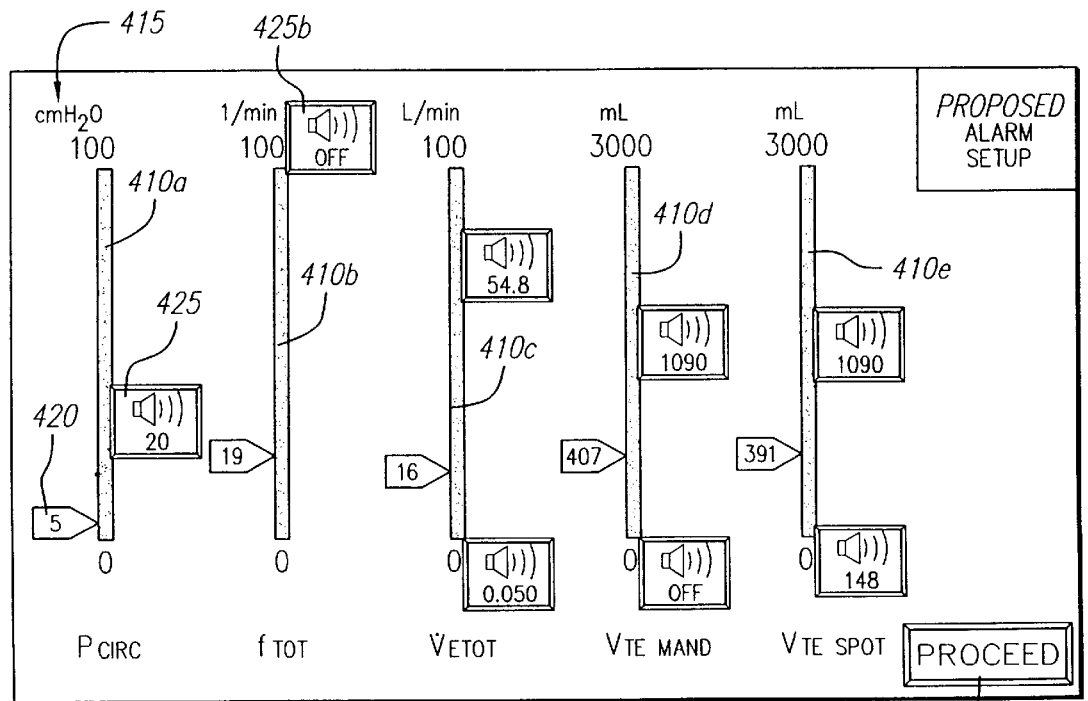
FIG. 10 is an illustration of an alarm setup screen including graphical representations of various alarms settings, acceptable alarm setting parameter ranges, and current patient data.

Referring now to FIG. 10, the alarm setup screen will be described. Touching the "Alarms" button 215 (FIG. 5) on the lower screen 70 causes the processor 30 to display the alarm setup screen 400. The alarm setup screen 400 displays graphical representations for those user-adjustable alarms that are appropriate given the values selected for the main control settings. Thus, a user may be presented only with alarm settings required by the ventilation strategy already entered and stored in the memory 35 of the graphic user interface 20. This facilitates setup and prevents errors or omissions due to information overload given the relatively small size of the information display area 160 on the lower screen 70 of the graphic user interface 20.

Ease of use is further enhanced in that each graphical representation 410a, 410b, 410c, 410d and 410e of an alarm includes a label 415 identifying the patient data parameter associated with the alarm and a display 420 of its current value. The value for the alarm setting associated with particular patient data parameter setting is displayed on an on-screen button 425. To further enhance the usefulness and comprehensibility of the graphical representations 410a, 410b, 410c, 410d and 410e, the processor 30 causes the alarm on-screen button 425 to be displayed at a location along the graphical line that is proportional to the value of the setting with respect to total length of the graphical line.

The user may adjust the setting of each of the displayed alarm settings by touching a selected alarm on-screen button, such as alarm button 425, and then rotating the knob 106 (FIG. 3) until the desired alarm setting is displayed on the alarm button 425. As the value for the alarm setting is changed by rotating the knob 106, the processor changes the position of the alarm button 425 along the graphical line, providing a visual display of the change to the user. The position of the displayed patient data parameter 420 is similarly adjusted.

Certain alarm settings may also be turned off so that no alarm sounds for selected control settings. One possible display of an alarm in the off state is shown by the location and display of the alarm on-screen button 425b.

Some patient data parameters may require the setting of both upper and lower alarm limit values defining a range of acceptable values beyond which a user desires an alarm to be given, as is depicted by the graphical representation 410c. Alternatively, as depicted by the graphical representation 410d, a lower limit alarm may be turned off by the user, while setting an upper limit alarm to a selected value. Similarly, the upper limit alarm may be turned off while a value for a lower limit alarm is set. When all of the alarms are set, the user may store the values for one, or all of the alarm settings in a batch manner by touching the PROCEED button 430 followed by pressing the off-screen ACCEPT key 104.

Figure 11:
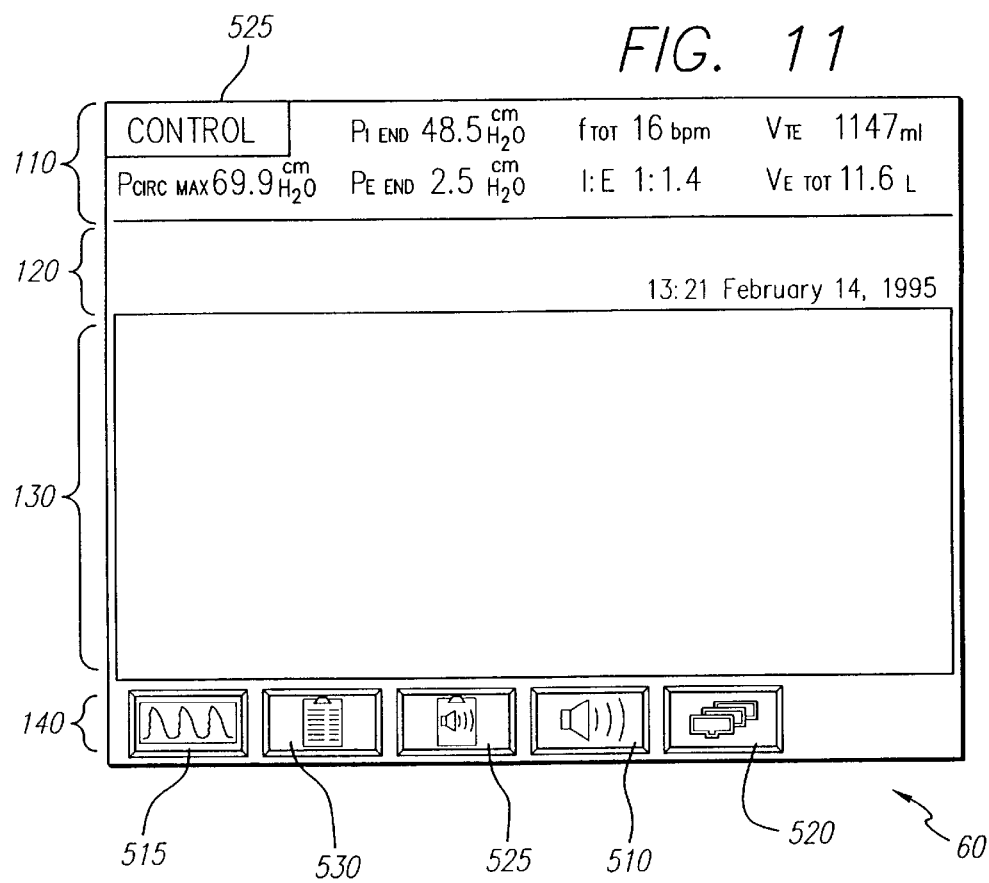
FIG. 11 is an illustration of the upper display screen of FIG. 3.

Referring now to FIG. 11, one exemplary layout of the upper display screen 60 of the graphic user interface 20 will now be described. As described above, the upper display screen 60 includes four non-overlapping areas 110, 120, 130 and 140. Generally, the upper display screen 60 provides a user with information regarding the state of the current ventilation therapy. Vital patient information is displayed in the vital patient information area 110. The information displayed in area 110 is always displayed when ventilation is in progress, even while the lower display screen 70 is being used to modify the settings controlling the ventilation. One novel aspect of the present invention is the display of the current breath type and breath phase in the breath type area 525 shown located in the upper left corner of the vital patient data area 110. In addition to the "CONTROL" breath type displayed, the ASSIST OR SPONT breath types may be displayed in accordance with the values for the main settings set as described above. The breath phase, that is, inspiration or expiration, is indicated by alternately reversing the display of the breath type in the breath type area 525. For example, the text displayed in the breath type area 525 may be displayed as black letters on a white background during the inspiration phase, and as white letters on a black background during the expiration phase.

It is not unusual during the course of a ventilation treatment session for values of monitored parameters to exceed the limits set for the various alarms that may be active during the session. The processor 30 receives signals from the sensors 27 (FIG. 2) for a variety of monitored parameters through the interface 32 and compares the values of those inputs to the values associated with the alarm settings stored in the memory 35. When the processor determines that the value of an input violates the value or values for the limit or limits for a particular alarm setting associated with that input stored in the memory 35, the processor 30 may cause an audible alarm to be sounded, and displays a text prompt identifying the monitored parameter, the cause of the alarm and a proposed course of action to correct the out of limit condition in the alarm messages area 120. If an event occurs that is potentially harmful to the patient, the processor 30 may also control the ventilator to abort delivery of the current breath until a user may intervene and correct the condition causing the alarm.

Many alarm conditions, however, may exist that do not require immediate correction, but are useful to evaluate the course of the respiratory treatment. Accordingly, all alarms are accumulated in an "Alarm Log" that is a chronological listing of all alarms that have occurred and which may be reviewed in area 130 of the upper screen 130 (FIG. 3) at any time during or after respiratory treatment. If, for some reason, the alarm log contains records of alarm conditions than may be conveniently stored for latter viewing, the processor 30 may cause the oldest alarm records to be deleted, and thus they will not be available for viewing.

Figure 12:
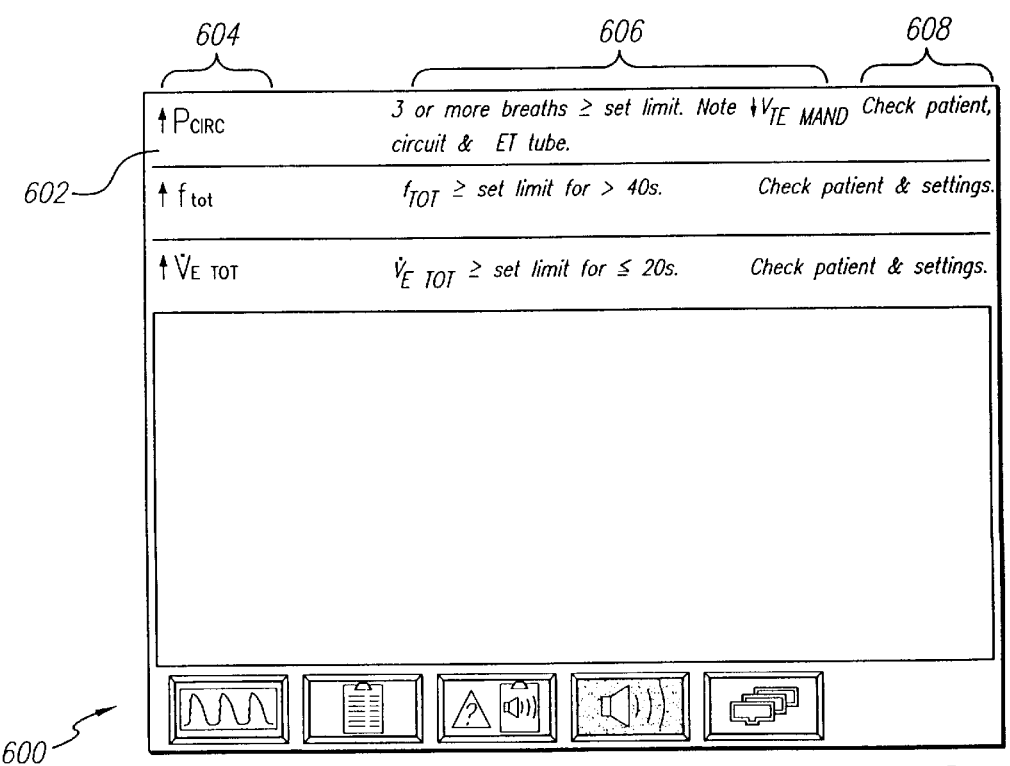
FIG. 12 is an illustration of a "More Alarms" display screen displayed within the information area of the display screen of FIG. 11.

If multiple alarm conditions occur during the course of treatment, the number of alarm messages may exceed the display area available in the alarm message display area 120. The processor 30 may display those alarms having the highest priority in the display area 120, scrolling alarms having a lower priority off the screen. The user may review alarms having a lower priority by touching the "More Alarms" button 510 displayed in the controls area 140. The scrolled alarm messages are displayed in the information area 130 of the upper screen 60. When the "More Alarms" button 510 is touched, the upper screen 60 is temporarily re-arrange to merge areas 130 and 120 into a combined and larger active alarms display, as depicted in FIG. 12. Touching the "More Alarms" button 510 again causes the processor 30 to redisplay the default screen display depicted in the FIG. 11.

Each alarm message 602 (FIG. 12) includes three messages to assist the user in correcting the cause of the alarm. A base message 604 identifies the alarm. As will be described more fully below, the user may touch the alarm symbol to display a definition of the alarm symbol in the symbol definition area 180 of the lower screen 70 (FIG. 3). An analysis message 606 gives the root cause of the alarm, and may also describe dependent alarms that have arisen due to the initial alarm. A remedy message 608 suggest steps that can be taken by the user to correct the alarm condition.

As illustrated above, the processor 30 may be responsive to user commands to display various kinds of information in the information area 130. For example, FIG. 11 depicts one possible embodiment of the upper screen 60 having five on-screen buttons for causing various information and data to be displayed in the information area 130. Touching "Waveform" button 515 causes the processor 30 to display a graphical plot of the data pertinent to the respiratory therapy being given to the patient. Similarly, touching the "More Data" button 530 results in the processor 30 displaying a screen including a variety of data that may be useful to the user in assessing the status of the patient and the progress of the ventilation therapy. It will be understood that the present invention is not limited to including only the five on-screen buttons depicted in FIG. 11. Because the on-screen buttons are implemented by the processor 30, with suitable programming the processor 30 may be enabled to display different or additional on-screen buttons and perform actions in response to their actuation.

Figure 13:
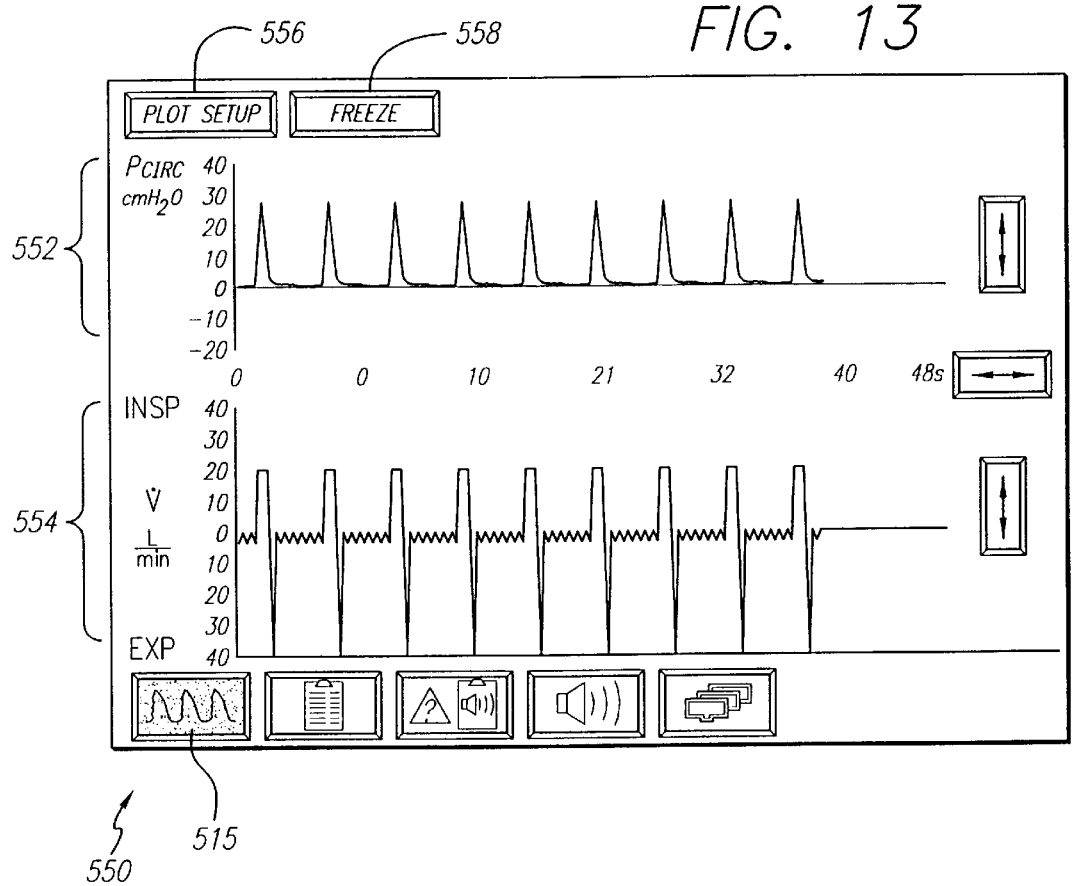
FIG. 13 is an illustration of a "Waveforms" display screen displayed within the information area of the display screen of FIG. 11.

Touching the "Waveform" button 515 displays a waveform display screen 550 as illustrated by FIG. 13. This display allows for real-time plotting of patient data in the tow plots areas 552 and 554. Different plots may be displayed in each of the plot areas 552 and 554. A plot setup screen (not shown) may be accessed by the user by touching the "Plot Setup" button 556. The user may select among plots of pressure versus time, volume versus time, flow versus time and pressure versus volume.

The waveform display screen 550 also includes a "Freeze" button 558 for freezing any waveform that is currently being plotted in either plot area 552 or 554. Touching button 558 causes a flashing "Freezing" message to be displayed until the current plot is completed and prevents any changes being made to the waveform display screen 550 by causing the various buttons controlling the scale of the displays, as well as buttons 556 and 558 to disappear. The only visible button is an "Unfreeze" button (not shown). When the current plot is complete, plotting stops and the on-screen buttons reappear.

Other displays may also be accessed by touching the on-screen buttons displayed in the controls area 140 of the upper screen 60. For example, touching the "Alarm Log" button 525 causes a screen listing all of the alarm events up to a predetermined maximum number of alarms, including those that have been corrected by the user, that have been sounded during therapy. Touching the "More Screens" button 520 causes the display of a set of additional on-screen buttons giving access to additional data not otherwise presented on the main display screens. This feature provides a flexible way to add new features and screens with minimal impact on the overall design of the graphic user interface.

Figure 14:
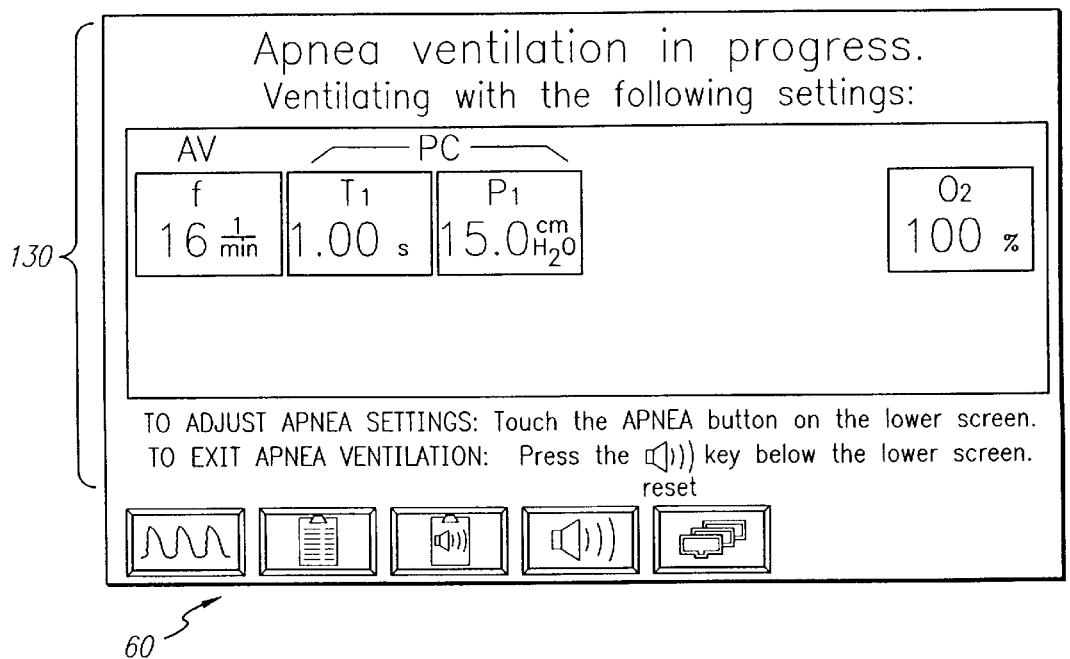
FIG. 14 is an illustration of an "Apnea Ventilation In Progress" display screen displayed within the information area of the display screen of FIG. 11.

In some modes of operation, the respirator processor 60 (FIG. 2) is responsive to signals received from a sensor 27 in the ventilator to provide inspiration. In this manner, the inspiration may be provided when the patient begins to draw a breath in, which is sensed by the sensor and results in the respirator processor 60 causing the ventilator to provide an inspiration. The respirator processor 60 may be programmed to monitor the rate at which a patient triggers the sensor, and, when that rate falls below a predetermined number of breaths per minute, the value of which may be stored in the memory 65 (FIG. 2), the respirator processor 60 sends a signal through the interface 32 to the processor 30 of the graphic user interface 20. In response to this signal, the processor 30 displays an "Apnea Ventilation In Progress" screen 600 in area 130 of the upper display 60, as depicted in FIG. 14. A variety of information may be displayed on this screen to inform the user of the status of the patient and the ventilation. For example, the main control settings and the ventilation settings currently active may be displayed along with a message indicating that apnea ventilation is in progress. Simultaneously, the respirator processor 60 switches to "Apnea" mode and provides breathing assistance to the patient.

Figure 15:
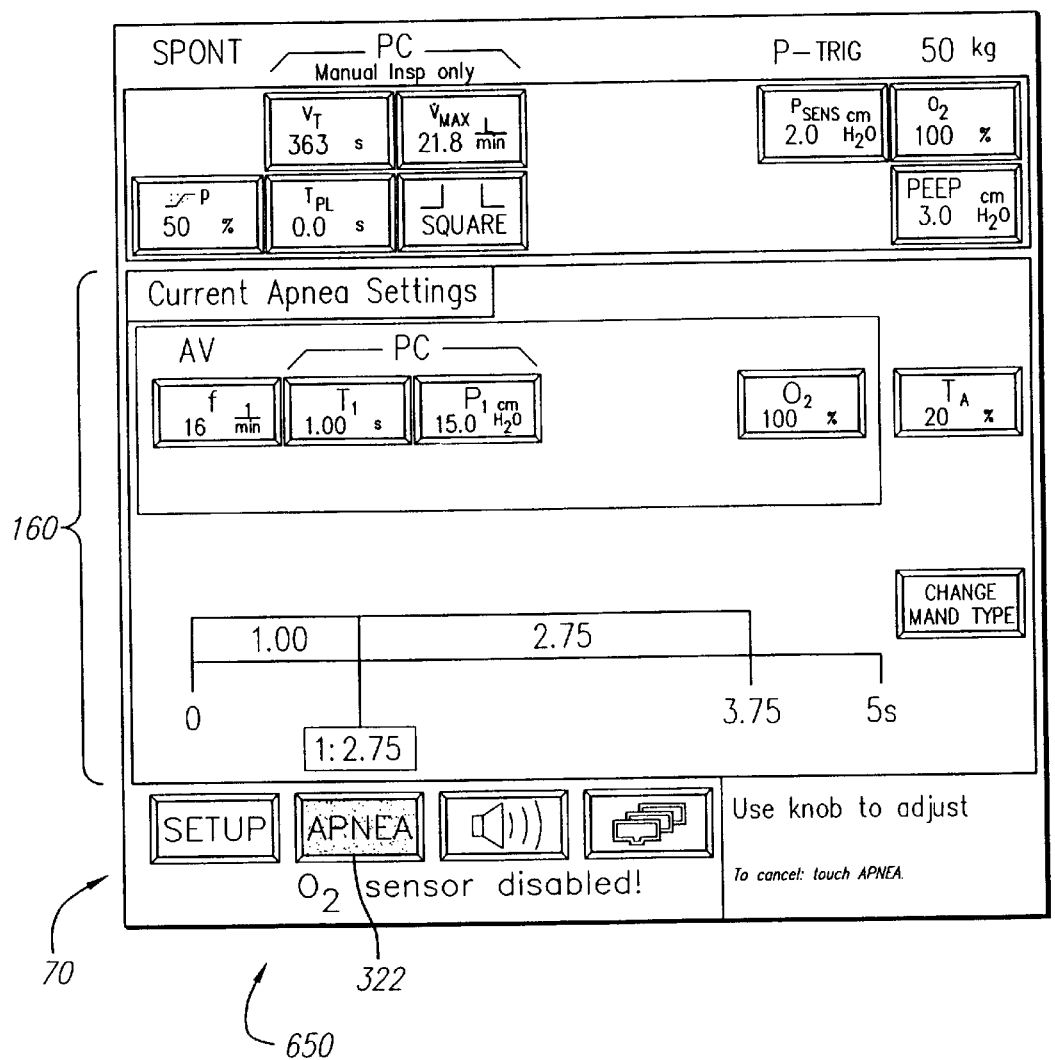
FIG. 15 is an illustration of an "Apnea Settings" display screen displayed within the information area of the lower display screen of FIG. 3.

When the respirator processor 60 automatically institutes "Apnea" mode in response to a lack of inspiration by the patient being treated, the respirator processor 60 controls the apnea ventilation using values of various settings entered by the user from an apnea setup screen 650 that may be displayed in the information area 160 of the lower screen 70 as depicted in FIG. 15 by touching the "Apnea" on-screen button 322 on the lower screen 70 of the graphic user interface 20. One useful feature of the manner in which the processor controls the displays of the graphic user interface is illustrated in FIG. 15. As is shown, the values for the main control settings and the on-screen buttons for setting the ventilation settings appropriate for those main control settings for the ventilation in process when "Apnea" mode was entered are displayed in areas 152 and 154 of the lower display screen (FIG. 5). Additionally, the current apnea settings are displayed in the information area 160, along with on-screen buttons which can be actuated in concert with the knob 106 to adjust the apnea settings.

Referring again to FIG. 5, another novel aspect of the present invention will now be described. The lower display screen 70 includes an area 180 in which the processor 30 may display a variety of messages to assist the user in setting up the graphic user interface. These messages may be different from, or in addition to prompts displayed by the processor 30 in the prompt area 190 of the lower display screen 70. One possible use of the area 180 is to provide a textual definition of a graphic symbol identifying a on-screen button. For example, when a user touches the "Waveform" on-screen button 515 on the upper display screen 60 (FIG. 11), the text "Waveform" may be displayed by the processor 30 in the display area 180. This feature provides the user with an easily accessible means to determine the functionality of any of the graphically identified on-screen buttons on either the upper or lower display screens 60, 70 while allowing the elimination of textual information from the displayed on-screen button to simplify the display.

It is generally an unsafe practice to power-up a ventilator with a patient already attached because the ventilator may attempt to ventilate the patient in a manner which would be harmful to the patient. The respirator processor 60 is responsive to detection of a such a condition to start an "Safety PCV" ventilation mode and to send a signal to the processor 30 of the graphic user interface 20 to sound an alarm. In this mode, the respirator processor 60 controls the respirator 22 using a pre-determined set of ventilator setting in pressure-control mode. These pre-determined settings are selected to safely ventilate the widest set of possible patients. Once the new patient, or same patient setup process is completed as described above, the processor terminates the "Safety PCV" mode, and begins ventilating the patient in accordance with the newly entered settings.

From the above, it may be seen that the present invention represents and improved graphic user interface which assists the user in the setup of ventilator strategy and parameters, while also providing an enhanced understanding of the setup procedure. The present invention also ensures that a patient is not ventilated using inappropriate ventilation parameters if the ventilator is started up with the patient already attached to the ventilator. While several forms of the invention have been illustrated and described, it will also be apparent that various modifications can be made without departing from the spirit and scope of the invention. Accordingly, it is not intended that the invention be limited, except by the appended claims.

We claim:

1. A method of powering up a patient ventilator, comprising:

connecting a ventilator to a source of power;

detecting if a patient is connected to the ventilator when the ventilator is initially powered up and prior to input of ventilator settings to the ventilator pertaining to said patient;

ventilating said patient in a safety mode in accordance with a stored set of ventilator parameter values, the stored set of ventilator parameter values having been selected to safely ventilate a majority of patients if said patient is connected to the ventilator when the ventilator is powered up;

providing ventilator parameter values to a ventilator controller, the ventilator parameters values being selected from a range of ventilator parameters values and stored in a memory of the ventilator controller; and providing breath support ventilation to the patient in response to the ventilator parameter values.

2. A method of starting up a patient ventilator from a powered down condition, comprising:

connecting a ventilator to a source of electrical power;

initiating a start up sequence of the ventilator, wherein said start up sequence comprises the steps of detecting if a patient is connected to the ventilator when the ventilator is initially powered up and prior to input of ventilator settings to the ventilator pertaining to said patient:

ventilating said patient in a safety mode in accordance with a stored set of ventilator parameter values, the stored set of ventilator parameter values having been selected to safely ventilate a predetermined range of patients if said patient is connected to the ventilator when the ventilator is powered up;

displaying a ventilator start up display, the ventilator start up display including graphics of a new patient button, a same patient button and a short self test button; and selecting and actuating either the new patient button, the same patient button or the short self test button.

3. The method of claim 2, further comprising: actuating the new patient button; and displaying a new patient set up screen.

4. The method of claim 2, further comprising:

actuating the same patient button; and displaying a ventilation settings screen, the ventilation settings screen including a plurality of values of ventilator parameters used in a previous ventilation session of the same patient.

5. The method of claim 3, wherein the step of displaying includes displaying an ideal body weight button for selecting a value for an ideal body weight of the patient on the new patient setup screen.

6. The method of claim 5, further comprising:

actuating the ideal body weight button;

displaying a stored value for the ideal body weight; and selecting a value for the ideal body weight of said patient, if different from the stored ideal body weight of said patient.

7. The method of claim 6, further comprising:

accepting the value for the ideal body weight of the patient; and displaying a ventilation settings screen having a plurality of buttons associated with ventilator parameters, the ventilator parameters having user selectable values.

8. The method of claim 7, wherein the step of displaying comprises displaying ventilator parameters determined to be appropriate for ventilating the patient as a function of the ideal body weight of the patient.

9. The method of claim 7, further comprising:

determining a range of values for each of the displayed ventilator parameters, the range of values being determined from the ideal body weight of the patient;

selecting one of the ventilator parameters to enable selection of a value for the selected parameter;

selecting the value for the selected parameters from the determined range of values for the selected parameter;

accepting the selected value for the selected parameter; and controlling the ventilator in accordance with the selected value.

10. The method of claim 9, wherein the step of selecting a value comprises actuating an override button to enable a user to select a value for the selected parameter that is not one of the values in the determined range of values for the selected parameter.

11. The method of claim 7, further comprising:

determining a range of values for each of the displayed ventilator parameters, the range of values being determined from the value of the ideal body weight of the patient;

selecting a first one of the ventilator parameters to enable selection of a value for the selected parameter;

selecting the value from the determined range of values for the selected parameter;

selecting a second one of the ventilator parameters;

selecting a value from the determined range of values for the selected second one of the ventilator parameters;

accepting the selected values of the first and second ventilator parameters; and controlling the ventilator according to the selected values.

12. The method of claim 11, wherein the steps of selecting values comprise actuating an override button to enable a user to select a value for the selected parameter that is not one of the values in the determined range of values for the selected parameter.

* * * * *

UNITED STATES PATENT AND TRADEMARK OFFICE
CERTIFICATE OF CORRECTION

PATENT NO. : 5,915,380
DATED : Jun. 29, 1999
INVENTOR(S) : Charles L. Wallace, Warren G. Sanborn, David Arnett, Howard L. Ferguson, Jay Butterbrodt, It is certified that error appears in the above-identified patent and that said Letters Patent is hereby corrected as shown below:

Drawing Sheet 2 of 9, FIG. 2, change "60" identifying the "RESPIRATOR PROCESSOR", to read --61--.

Drawing Sheet 3 of 9, FIG. 3, change "20" identifying the display panel, to read --50--.

Column 6, line 15, change "30", to read --35--.

Column 6, line 27, change "60", to read --61--.

Column 6, line 32, change "20", to read --10--.

Column 6, line 39, change "60", to read --61--.

Column 8, line 42, change "20", to read --10--.

Signed and Sealed this

Twenty-ninth Day of February, 2000

Attest:

Q. TODD DICKINSON

*Attesting Officer*  *Commissioner of Patents and Trademarks*